US006248566B1

(12) United States Patent
Imanaka et al.

(10) Patent No.: US 6,248,566 B1
(45) Date of Patent: Jun. 19, 2001

(54) GLUCAN HAVING CYCLIC STRUCTURE AND METHOD FOR PRODUCING THE SAME

(75) Inventors: Tadayuki Imanaka, Suita; Yoshinobu Terada, Osaka; Takeshi Takaha, Kobe; Michiyo Yanase, Hyogo-ken; Shigetaka Okada, Ikoma; Hiroki Takata, Kobe; Hiroyasu Nakamura; Kazutoshi Fujii, both of Amagasaki, all of (JP)

(73) Assignee: Ezaki Glico Co., Ltd., Osaka (JP)

( * ) Notice: Subject to any disclaimer, the term of this patent is extended or adjusted under 35 U.S.C. 154(b) by 0 days.

(21) Appl. No.: 08/528,026

(22) Filed: Sep. 13, 1995

Related U.S. Application Data

(63) Continuation-in-part of application No. 08/415,152, filed on Mar. 31, 1995, now Pat. No. 5,686,132.

(30) Foreign Application Priority Data

Sep. 13, 1994 (JP) .................................................. 6-218554
Jul. 31, 1995 (JP) .................................................. 7-195647

(51) Int. Cl.$^7$ .................................................. C12P 19/00
(52) U.S. Cl. .................................................. 435/72; 536/1.11
(58) Field of Search .................................. 435/72, 73, 74

(56) References Cited

U.S. PATENT DOCUMENTS 5,364,936  11/1994  Oguma et al. ........................ 536/103

FOREIGN PATENT DOCUMENTS

| 52-25043 | 2/1977 | (JP) . |
| 54-43246 | 4/1979 | (JP) . |
| 60-75295 | 4/1985 | (JP) . |
| 63-46201 | 2/1988 | (JP) . |
| 64-74997 | 3/1989 | (JP) . |
| 6-62883  | 3/1994 | (JP) . |

OTHER PUBLICATIONS

French et al., "Studies on the Schardinger Dextrins," *Archives of Biochemistry and Biophysics* 111:153–160 (1965).
Kobayashi, "Fundamental Study and Application of Cyclodextrins," *Denpun Kagaku* 40(2):103–116 (1993).
Horikoshi et al., "Industrial Production of Cyclodextrins," *I. Int. Symp. on Cyclodextrins* 25–39 (1981).
*Denpun Kagaku* 38:314 (1991).
Endo et al., "Isolation, Purification and Characterization of Cyclomaltododecaose (η–cyclodextrin)," *Carbohydrate Res.*, 269:369–373 (1995).
French, "The Schardinger Dextrins," Dept. of Chemistry, Iowa State College, Ames, Iowa, pp. 189–260.
Matsuura et al., "Crystal Structure of Cyclodextrin Glucanotransferase from *Bacillus stearothermophilus* and its Carbohydrate Binding Sites," *Enzyme Chemistry and Molecular Biology of Amylases*, pp. 153–162.
Pulley et al., "Studies on the Schardinger Dextrins. The Isolation of New Schardinger Dextrins," *Biochemical and Biophysical Res. Comm.* 5:(1):11–15 (1961).
Sundararajan et al., "Conformational Studies on Cycloamyloses," *Carbohydrate Res.* 13:351–358 (1970).
French, D., et al., "Studies on the Schardinger Dextrins," *Archives of Biochemistry and Biophysics*, 1965, 111, pp. 153–160.
Oguma, T., et al., "Purification and properties of a novel enzyme from Bacillus spp. T–3040, which catalyzes the conversion of dextran to cyclic isomaltooligosaccharides," *FEBS Letters*, 1994, 345, pp. 135–138.
Schmid, Gerhard, "Cyclodextrin glycosyltransferase production: yield enhancement by overexpression of cloned genes," *TIBTECH*, Sep. 1989, vol. 7, pp. 244–248.

*Primary Examiner*—Elli Peselev
(74) *Attorney, Agent, or Firm*—Bozicevic & Reed LLP

(57) ABSTRACT

Glucan with a degree of polymerization of 50 or more includes an inner branched cyclic structure portion and an outer branched structure portion, and methods for producing the same.

11 Claims, 15 Drawing Sheets

|  | Conserved region 1 | Conserved region 2 | Conserved region 3 | Conserved region 4 |
|---|---|---|---|---|
| α-amylase | DAVINH | GFRLDAAKH | EVID | FVDNHD |
| Branching enzyme |  |  |  |  |
| Derived from E. coli | DWVPGHF | ALRVDAVAS | EFGG | LPLSHDEVVH |
| Derived from Bacillus stearothermophilus 1503R-var. 4 | DWVPGHF | GFRVDAVAN | EFLQ | LPFSHDEVVH |

Primer 1    5'GAYTGGGTNCCNGSNCAYTTY3'
Primer 4                    3'WSNGTRCTRCTYCANCANGTR'

The amino acid sequence with solidline corresponds to
a DNA sequence of Primer 1, and the amino acid sequence
with wave line corresponds to a DNA sequence of Primer 4.
Y:T or C   N:G or A or T or C   S:G or C   W:A or T   R:A or G

FIG. 9

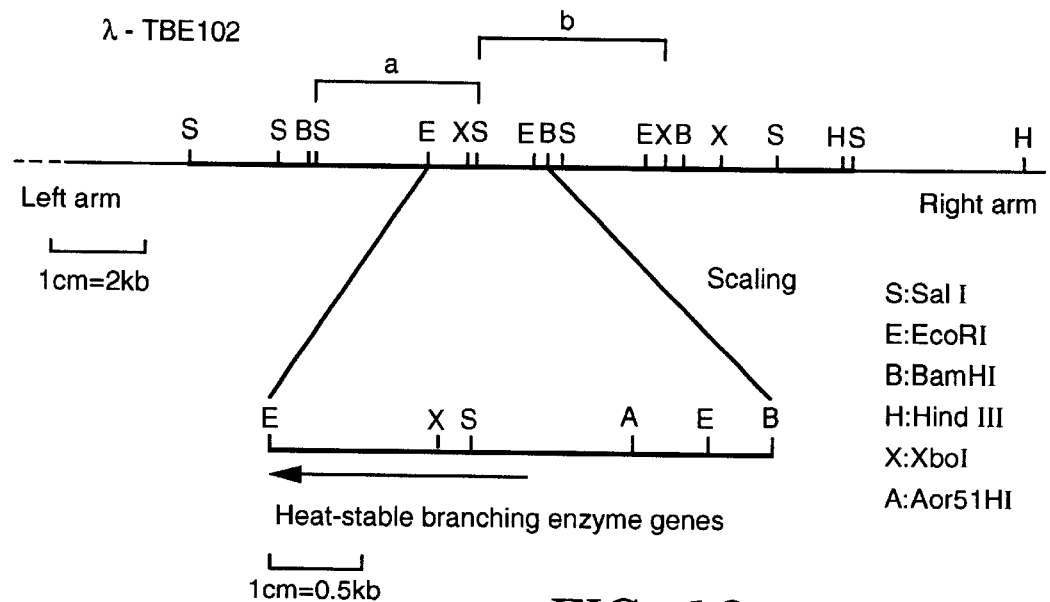

FIG. 10

GLUCAN HAVING CYCLIC STRUCTURE AND METHOD FOR PRODUCING THE SAME

CROSS-REFERENCE TO RELATED APPLICATION

This application is a continuation-in-part of U.S. patent application Ser. No. 08/415,152, filed Mar. 31, 1995, now U.S. Pat. No. 5,686,132.

BACKGROUND OF THE INVENTION

1. Field of the Invention

The present invention relates to glucan or derivatives thereof useful as raw materials in the starch processing industry, as a composition for drinks and foods, as a composition for food additives, as a composition for adhesion, or as starch substitutes for biodegradable plastic; and a method for producing the glucan or derivatives thereof.

More specifically, the present invention relates to glucan with a degree of polymerization of 50 or more having an inner branched cyclic structure portion and an outer branched structure portion and a method for producing the same.

2. Description of the Related Art

Starch is a polymer substance used as a material for producing maltose, starch syrups, or cyclodextrin, a composition for foods and drinks, a composition for food additives, and a material for adhesion or biodegradable plastic. However, existing starch has various problems. For example, it is likely to retrograde and it has high viscosity. In general, starch has low solubility in water, and starch is therefore required to be heat treated or treated with an organic solvent, acid, or alkali so as to be dissolved in water.

Dissolved starch or gelatinized starch rapidly retrogrades to form an insoluble precipitate. When starch is retrograded, its physical properties such as viscoelasticity, adhesion change, water holding ability, shape holding properties, freezing resistance, and/or digestiveness in foods containing the retrograded starch decrease.

Furthermore, gelatinized starch has high viscosity. This is due to the fact that amylopectin in starch is composed of long chain molecules having a number of branches. In the case where maltose or cyclodextrin is produced using starch as a raw material, gelatinized starch is difficult to handle because of its high viscosity. For example, when gelatinized starch having a concentration at a certain level is transported through a pipe, the pipe becomes clogged with starch.

As described above, the characteristics (low solubility, retrogradation, and high viscosity) of existing starch limit the use thereof in foods and other fields.

Under these circumstances, a study was conducted for improving the solubility and retrogradation resistance of starch by allowing the starch to decompose into smaller molecules. As a result, retrogradation of starch was suppressed to a certain degree. However, it is difficult to prevent an excess decrease in molecular weight, and intrinsic characteristics of starch, which is originally a macromolecule, are lost. Furthermore, according to these methods, the reducing power of starch increases. When such starch is heated while being mixed with protein and amino acid so that when starch reacts, it turns colors. This problem also limits the use of starch.

On the other hand, a study for improving the solubility of starch without decomposing it into smaller molecules was conducted. Branching enzyme (Q-enzyme, EC 2.4.1.18) cleaves an α-1,4-bond of starch and allows an α-1,6-bond to be synthesized with the resulting starch by its transglycosylation reaction. Branching enzyme was allowed to react with starch to obtain water-soluble starch (Japanese Laid-Open Patent Publication No. 60-75295). However, the water-soluble starch obtained by this method is a polymer substance having a molecular weight, as high as starch used as a raw material, and therefore, cannot solve the problems mentioned above.

As a substitute for the above-mentioned starch, cyclic sugars composed of D-glucose, that is, cyclic glucan has been considered.

Cyclodextrins (CD) are known cyclic gulcans. Cyclodextrins are produced by allowing cyclodextrin glucanotransferase (hereafter, referred to as CGTase) to react with starch or the like. When CGTase is allowed to react with starch, cyclodextrins (α-CD, β-CD, and γ-CD) having a degree of polymerization of 6 to 8, respectively, are usually produced. α-CD, β-CD, and γ-CD cannot, however, be substitutes for starch; thus, cyclodextrin having a higher degree of polymerization is desired.

Cyclodextrins having a degree of polymerization of 9 to 13 are synthesized by allowing CGTase to react with starch (Archives of Biochemistry and Biophysics, vol. 111, pp. 153–165 (1965)); however, their yield is extremely low.

Although Japanese Laid-Open Patent Publication No. 6-62883 discloses CD having a high degree of polymerization, its degree of polymerization is as high as 28. Furthermore, Archives of Biochemistry and Biophysics, vol. 111, pp. 153–165 (1965) describes that glucan (inner branched glucan or inner branched CD) having an α-1,6-bond in a cyclic structure composed of an α-1,4-glucoside bond, or glucan (outer branched glucan or outer branched CD) having an α-1,6-bond outside of a cyclic α-1,4-glucan is produced as a by-product of the action of CGTase on starch.

Japanese Laid-Open Patent Publication No. 6-62883 describes the structure of inner branched glucan by illustrating cyclodextrin having an inner branched structure. This Publication describes that inner branched cyclodextrin is present only in large cyclic cyclodextrin having degree of polymerization of 10 to 13 in which large strain is applied; and that the number of α-1,6-bonds present in the ring was one in accordance with analysis.

Japanese Laid-Open Patent Publication Nos. 63-46201 and 64-74997 describe the structure of an outer branched glucan and the method for producing the same. These Publications describe that branched dextrin can be produced by reacting debranching enzyme with the mixture of cyclodextrin and linear or branched dextrin. However, since cyclodextrin used for the reaction has no inner branched cyclic structure, glucan having an inner branched cyclic structure portion and an outer branched structure portion are not disclosed. Furthermore, the cyclic structure portion has a degree of polymerization of 6 to 8, and the outer branched structure portion is merely bound by maltooligosaccharide or branched maltooligosaccharide having a degree of polymerization of as high as 6.

As described above, although cyclodextrin may be considered a substitute for the above-mentioned starch, the CDs above cannot be a substitute for starch because of their small degree of polymerization. Although inner branched or outer branched CDs are disclosed, those branched CDs also have small degree of polymerization, and they are products of trace yields, so that they cannot be used as a substitute for starch.

In view of the above-mentioned circumstances, a method for easily producing cyclic glucan having a large molecular weight capable of being a substitute for starch is desired.

SUMMARY OF THE INVENTION

A glucan with a degree of polymerization of 50 or more according to this invention includes an inner branched cyclic structure portion and an outer branched structure portion.

In one embodiment of the invention, the degree of polymerization of the glucan is in the range of 50 to 5,000.

In another embodiment of the invention, a degree of polymerization of the inner branched cyclic structure portion is in the range of 10 to 100.

In another embodiment of the invention, a degree of polymerization of the outer branched structure portion is 40 or more.

In another embodiment of the invention, a degree of polymerization of each unit chain of the outer branched structure portion is in the range of 10 to 20 on average.

Alternatively, the present invention includes a mixture of glucans with a degree of polymerization of 50 or more having an inner branched cyclic structure portion and outer branched structure portion and glucan having a cyclic structure consisting of only α-1,4-glucoside bonds.

According to another aspect of the invention, a method for producing glucan with a degree of polymerization of 50 or more including an inner branched cyclic structure portion and an outer branched structure portion, includes the step of: allowing a carbohydrate containing α-1,4-glucoside bonds and at least one α-1,6-glucoside bond to react with an enzyme capable of acting on the carbohydrate to form a cyclic structure.

In one embodiment of the invention, the carbohydrate is starch.

In another embodiment of the invention, the carbohydrate is amylopectin.

In another embodiment of the invention, the enzyme is a branching enzyme.

In another embodiment of the invention, the enzyme is a D-enzyme.

In another embodiment of the invention, the enzyme is cyclodextrin glucanotransferase.

In another embodiment of the invention, the cyclodextrin glucanotransferase is an enzyme derived from *Alkalophilic Bacillus* sp. A2-5a.

In another embodiment of the invention, the degree of polymerization of the glucan is in the range of 50 to 5,000.

In another embodiment of the invention, a degree of polymerization of the inner branched cyclic structure portion of the glucan is in the range of 10 to 100.

In another embodiment of the invention, a degree of polymerization of the outer branched structure portion is 40 or more.

In another embodiment of the invention, a degree of polymerization of each unit chain of the outer branched structure portion of the glucan is in the range of 10 to 20 on average.

Alternatively, a method for producing glucan with a degree of polymerization of 50 or more including an inner branched cyclic structure portion and an outer branched structure portion, includes the step of: allowing a carbohydrate consisting of only α-1,4-glucoside bonds to react with a branching enzyme.

Alternatively, a method for producing a mixture comprising glucan having a degree of polymerization of 50 or more including an inner branched cyclic structure portion and an outer branched structure portion and glucan having a cyclic structure containing only α-1,4-glucoside bonds, includes the step of: allowing a carbohydrate containing α-1,4-glucoside bonds and at least one α-1,6-glucoside bond to react with an enzyme capable of acting on the carbohydrate to form a cyclic structure.

In one embodiment of the invention, the carbohydrate is starch.

In another embodiment of the invention, the carbohydrate is amylopectin.

In another embodiment of the invention, the enzyme is a D-enzyme.

In another embodiment of the invention, the enzyme is cyclodextrin glucanotransferase.

According to another aspect of the invention, a composition for foods and drinks of the present invention includes the above-mentioned glucan.

According to another aspect of the invention, a composition for food additives of the present invention includes the above-mentioned glucan.

According to another aspect of the invention, an infusion composition of the present invention includes the above-mentioned glucan.

According to another aspect of the invention, a composition for adhesion of the present invention includes the above-mentioned glucan.

According to another aspect of the invention, an anti-retrogradation agent of the present invention includes the above-mentioned glucan.

Thus, the invention described herein makes possible the advantages of providing cyclic glucan, which is a material useful as a substitute for starch, having outstanding properties such as higher solubility in water, lower viscosity when being dissolved to form a solution, and not decomposing unlike ordinary starch; and a novel method for producing the cyclic glucan.

These and other advantages of the present invention will become apparent to those skilled in the art upon reading and understanding the following detailed description with reference to the accompanying figures.

BRIEF DESCRIPTION OF THE DRAWINGS

FIG. 4 is schematic diagrams showing the conventionally considered reaction of CGTase.

FIG. 9 shows amino acid sequences of Conserved Regions 1 and 4 among various amylases, and oligonucleotide primers for cloning branching enzyme corresponding to these sequences.

FIG. 10 is a diagram showing a restriction enzyme map of λ-TBE102 containing branching enzyme gene.

DESCRIPTION OF THE PREFERRED EMBODIMENTS

Hereinafter, the present invention will be described in detail.

Outline of the Present Invention

Figure 1:
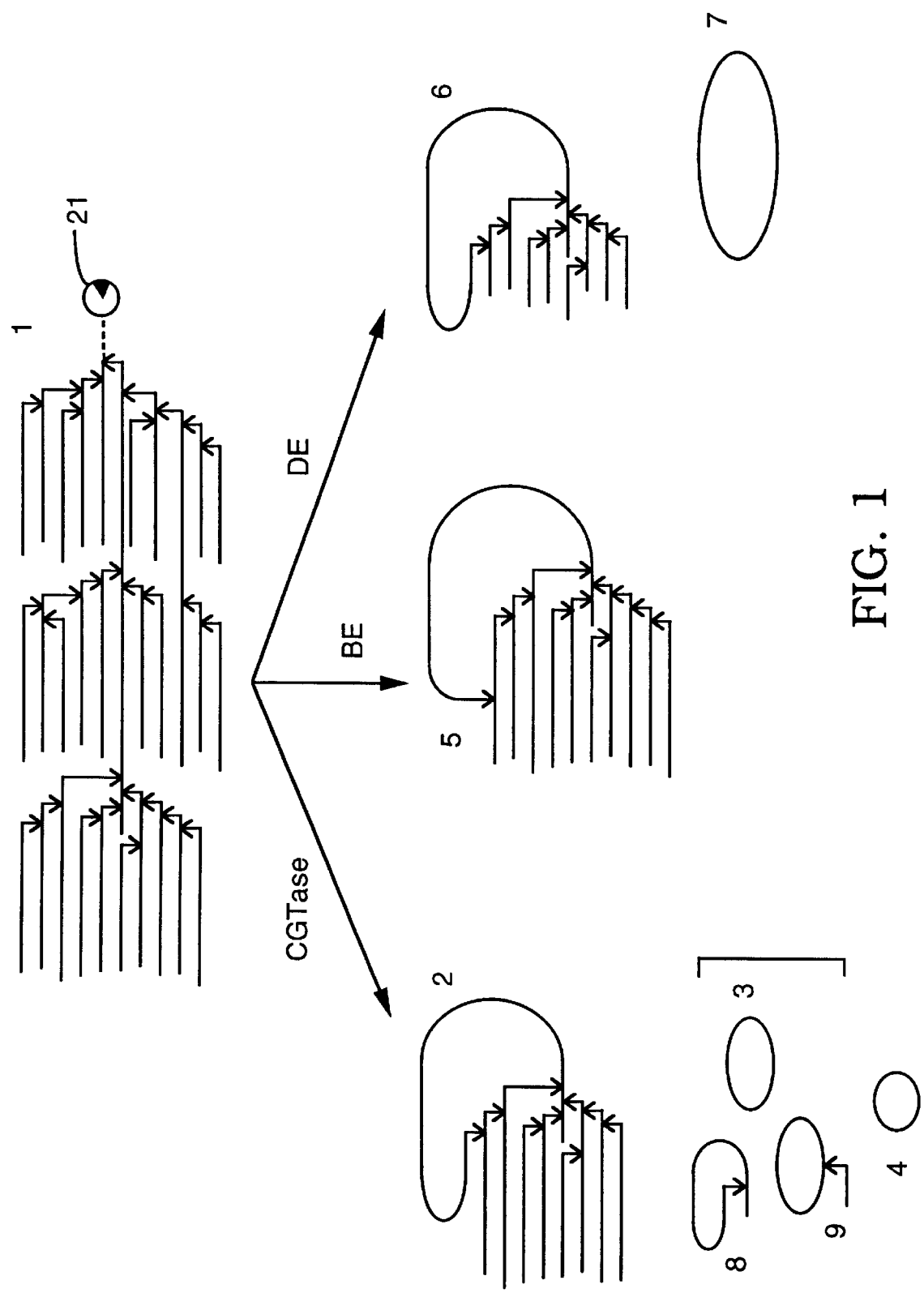
FIG. 1 is a schematic diagram illustrating an example of methods for producing glucan having an inner branched cyclic structure portion and an outer branched structure portion the present invention.

FIG. 1 is a schematic diagram showing an example of methods for producing glucan with a degree of polymerization of 50 or more having an inner branched cyclic structure portion and an outer branched structure portion. In FIG. 1, a straight line in a horizontal direction and a curve represent α-1,4-glucan chains, and an arrow in a vertical direction represents α-1,6-glucoside bonds. The reference numeral 21 denotes a reducing end. A white triangle represents a glucoside bond attacked by enzyme, and a black triangle represents a glucoside bond newly synthesized by enzymatic action. In schematic diagrams described below, the straight line in the horizontal direction and the curve, the arrow in the vertical direction, the white triangle, and the black triangle respectively represent the same components as shown in FIG. 1.

Figure 2:
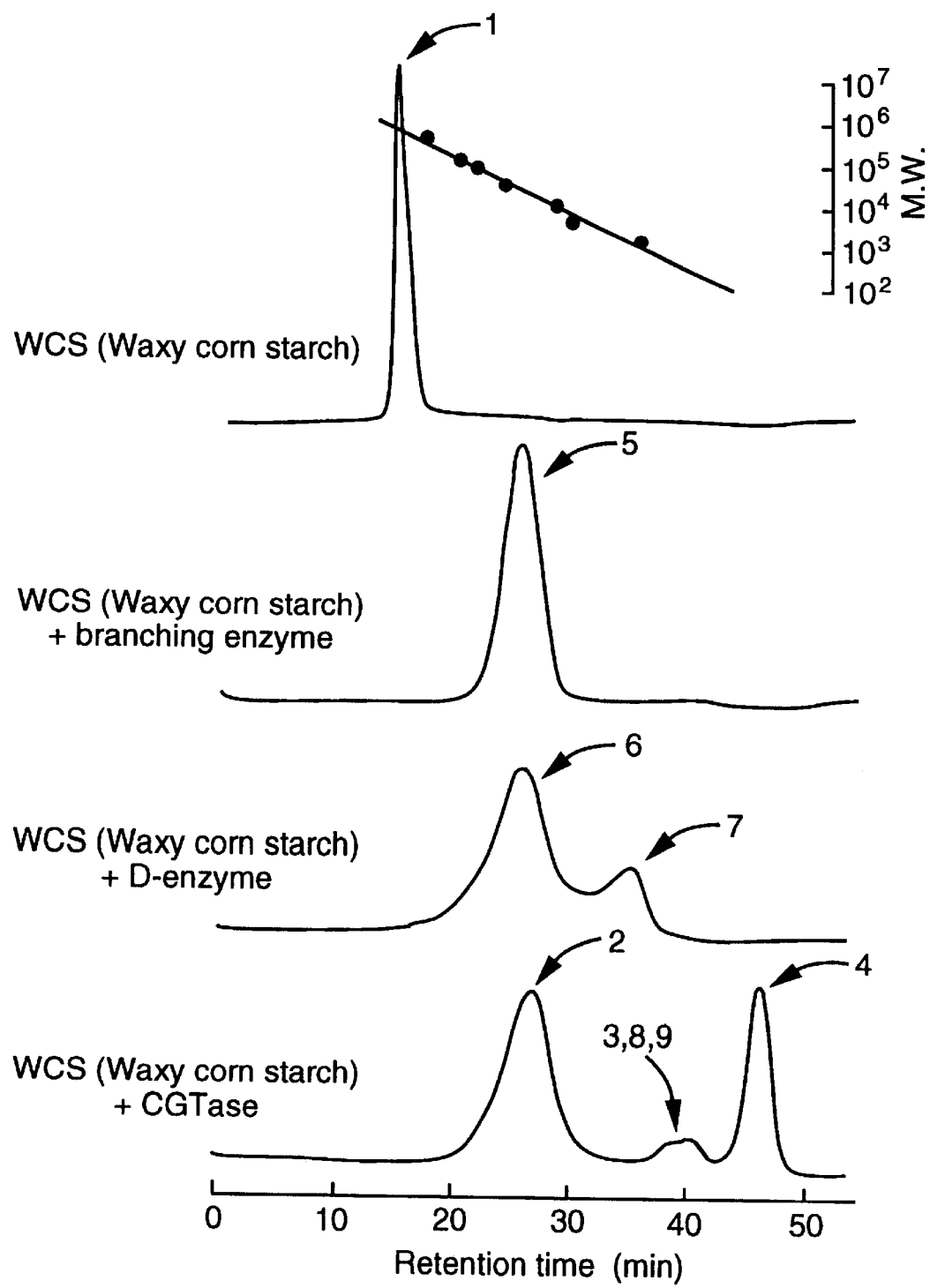
FIG. 2 shows gel filtration patterns of a reaction products obtained by the methods illustrated in FIG. 1.

The present invention is achieved based on the finding that when CGTase, branching enzyme (BE), or D-enzyme (DE) acts on amylopectin having α-1,4-glucoside bonds and α-1,6-glucoside bonds, glucan with a degree of polymerization of 50 or more having an inner branched cyclic structure portion and an outer branched structure portion denoted by the reference numerals 2, 5, and 6 in FIG. 1 are obtained. FIG. 2 shows gel filtration patterns of the reaction products obtained in FIG. 1. These reaction products have molecular weights which are much smaller than that of a material and larger than those of large cyclic CD represented by the reference numeral 3 of FIG. 1, an inner branched CD denoted by the reference numeral 8 of FIG. 1, an outer branched CD denoted by the reference numeral 9 of FIG. 1, a CD denoted by the reference numeral 4 of FIG. 1, and the like.

Figure 3:
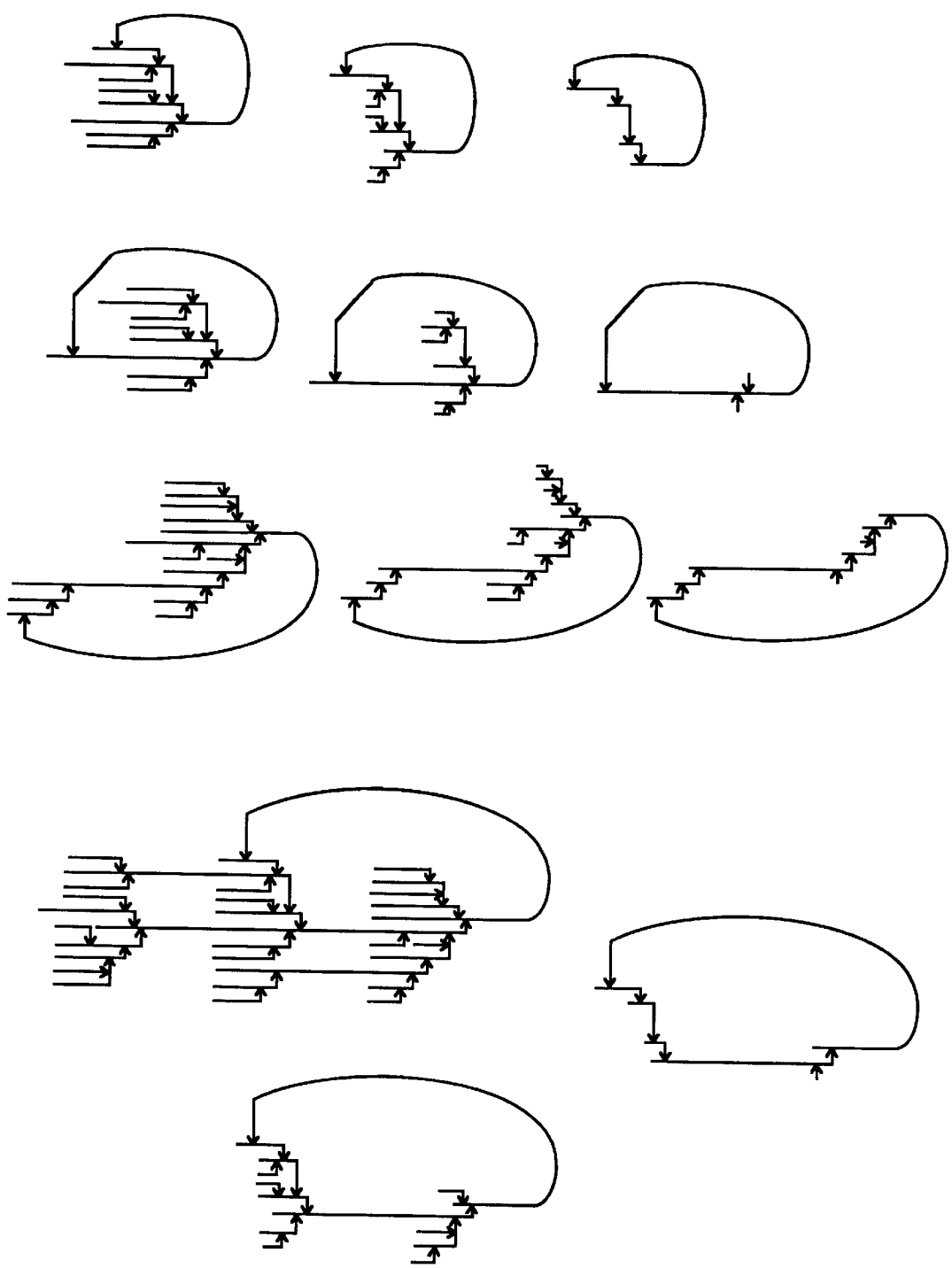
FIG. 3 is a schematic diagram illustrating embodiment of glucans obtained by the method according to the present invention.

As denoted by the reference numerals 2, 5, or 6 in FIG. 1, the glucan obtained by the method of the present invention has a degree of polymerization of 50 or more and is composed of an inner branched cyclic structure portion and an outer branched structure portion bound to the cyclic structure. FIG. 3 shows embodiments of the present invention.

In the present specification, the inner branched cyclic structure portion refers to a cyclic structure portion formed from α-1,4-glucoside bonds and at least one α-1,6-glucoside bond.

In the present specification, the outer branched structure portion refers to a non-cyclic structure portion bound to the inner branched cyclic structure portion.

In the present invention, the above-mentioned term "glucan" includes glucan and derivatives thereof. Furthermore, according to the method of the present invention, the term "material" includes derivatized materials.

Enzyme

As the enzyme used in the present invention, any enzymes capable of acting on carbohydrate having α-1,4-glucoside bonds and at least one α-1,6-glucoside bond to form glucan having a cyclic structure with a degree of polymerization of 50 or more can be used. Examples of the enzyme include 1,4-α-glucan branching enzyme (branching enzyme, Q-enzyme), 4-α-glucanotransferase (D-enzyme, amylomaltase, disproportionating enzyme), and cyclodextrin glucanotransferase (CGTase). However, the enzyme is not limited to these examples.

Considering the conventionally known action mechanism of the enzymes, it is surprising and unexpected that these enzymes produce glucan with a degree of polymerization of 50 or more having an inner branched cyclic structure portion and an outer branched structure portion.

Branching enzymes transfer a part of an α-1,4-glucan chain of starch-based carbohydrates to any C6 position of glucosyl residue of the glucan to form new α-1,6-linked branch. Thus, it was not expected that the branching enzyme would be capable of forming a cyclic structure.

Furthermore, D-enzyme (disproportionating enzyme) (EC 2.4.1.25) catalyzes glucan transfer reaction (disproportionation reaction) of maltooligosaccharide and transfer a glucosyl group, or maltosyl or maltooligosyl unit from a non-reducing end of a donor molecule to a non-reducing end of an acceptor molecule. Thus, as a result of the enzymatic reaction, the disproportionation of the degree of polymerization of initially provided maltooligosaccharide occurs. It is known that this disproportionating reaction occurs, when high molecular weight starch such as soluble starch or amylose is a donor, and glucose or maltooligosaccharide is an acceptor. Therefore, in the case where D-enzyme is allowed to act on starch, it can be expected that sugar having different degrees of polymerization would be generated; however, it cannot be expected that the D-enzyme would be capable of forming cyclic sugar, in the same manner as in branching enzyme.

It was also made clear that CGTase has a novel reaction mechanism which is different from that conventionally believed. Based on this fact, the present invention was achieved. Thus, according to the present invention, a novel method for producing cyclic glucan by using an enzyme, with which was considered heretofore to be impossible to produce glucan with a high degree of polymerization having a cyclic structure, is provided. Hereinafter, a novel reaction of CGTase will be described.

The conventionally considered reaction of CGTase will be described with reference to FIG. 4.

Figure 4B:
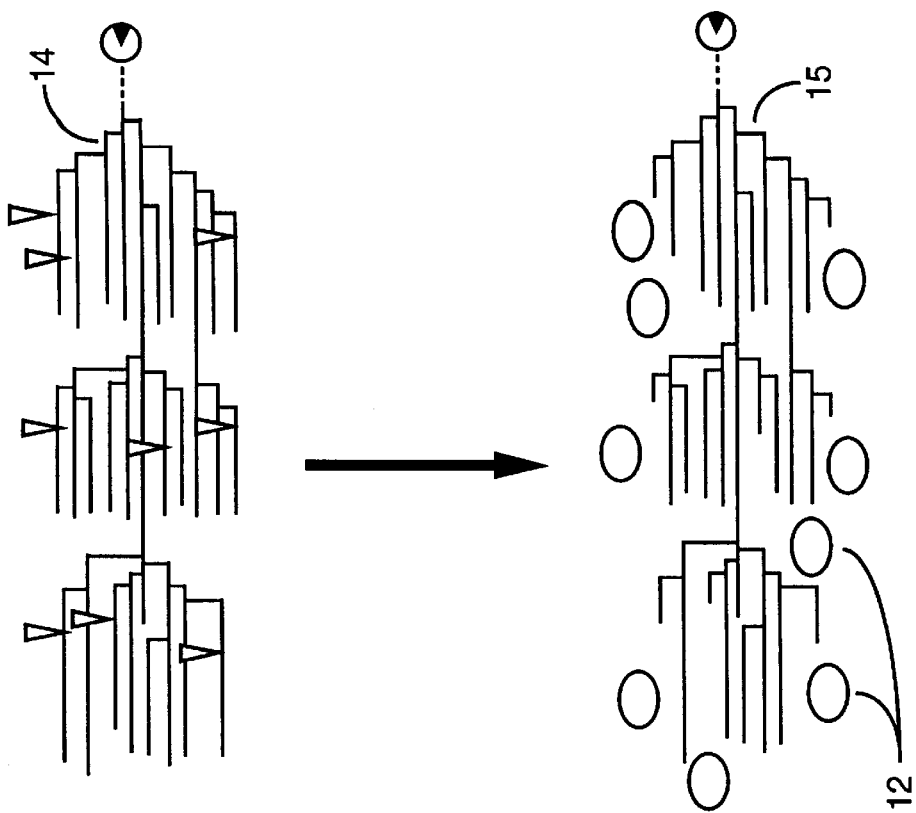
FIG. 4B shows the case where CGTase is allowed to act on amylopectin.
Figure 4A:
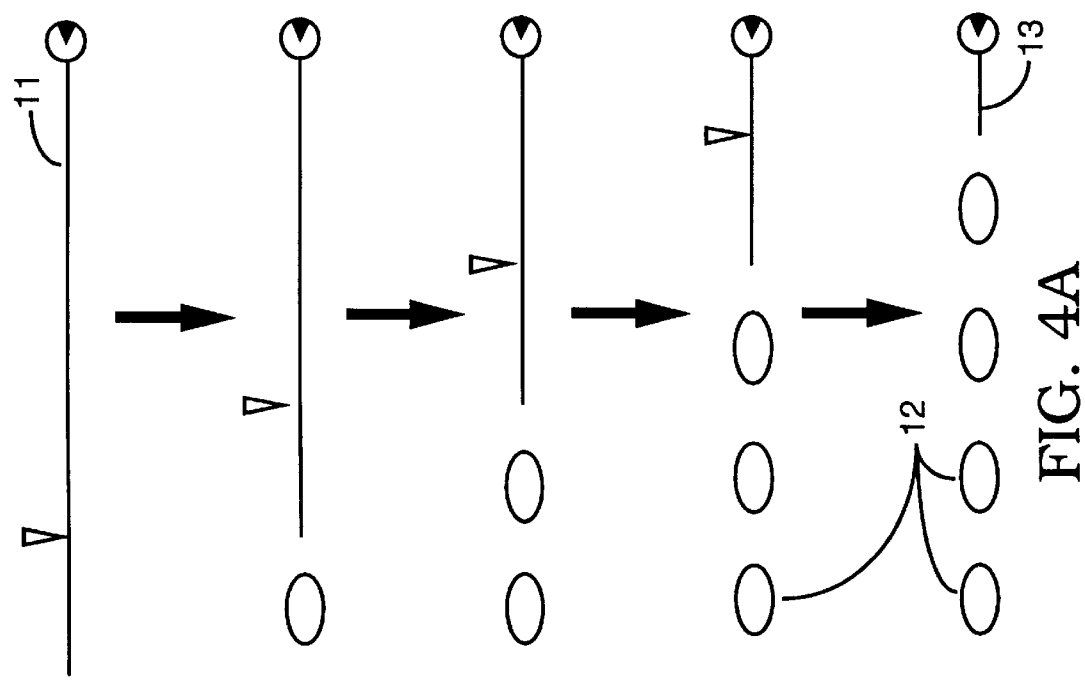
FIG. 4A shows the case where CGTase is allowed to act on amylose.

As shown in FIG. 4A, in the case where CGTase is allowed to act on α-1,4-glucan such as amylose 11, this enzyme recognizes 6 to 8 glucosyl units from a non-reducing end of an amylose molecule and cyclize these recognized portions. Final products from an original substrate are cyclic maltooligosaccharide (α-, β- and γ-CD) 12 and a small amount of non-cyclic oligosaccharide ride 13.

As shown in FIG. 4B, in the case where CGTase is allowed to act on amylopectin 14, this enzyme also recognizes 6 to 8 glucosyl units from a non-reducing end of an amylopectin side chain and cyclize these recognized portions. Final products from the original substrate are CD 12 having a degree of polymerization of 6 to 8 and non-cyclic limit dextrin 15.

Figure 5:
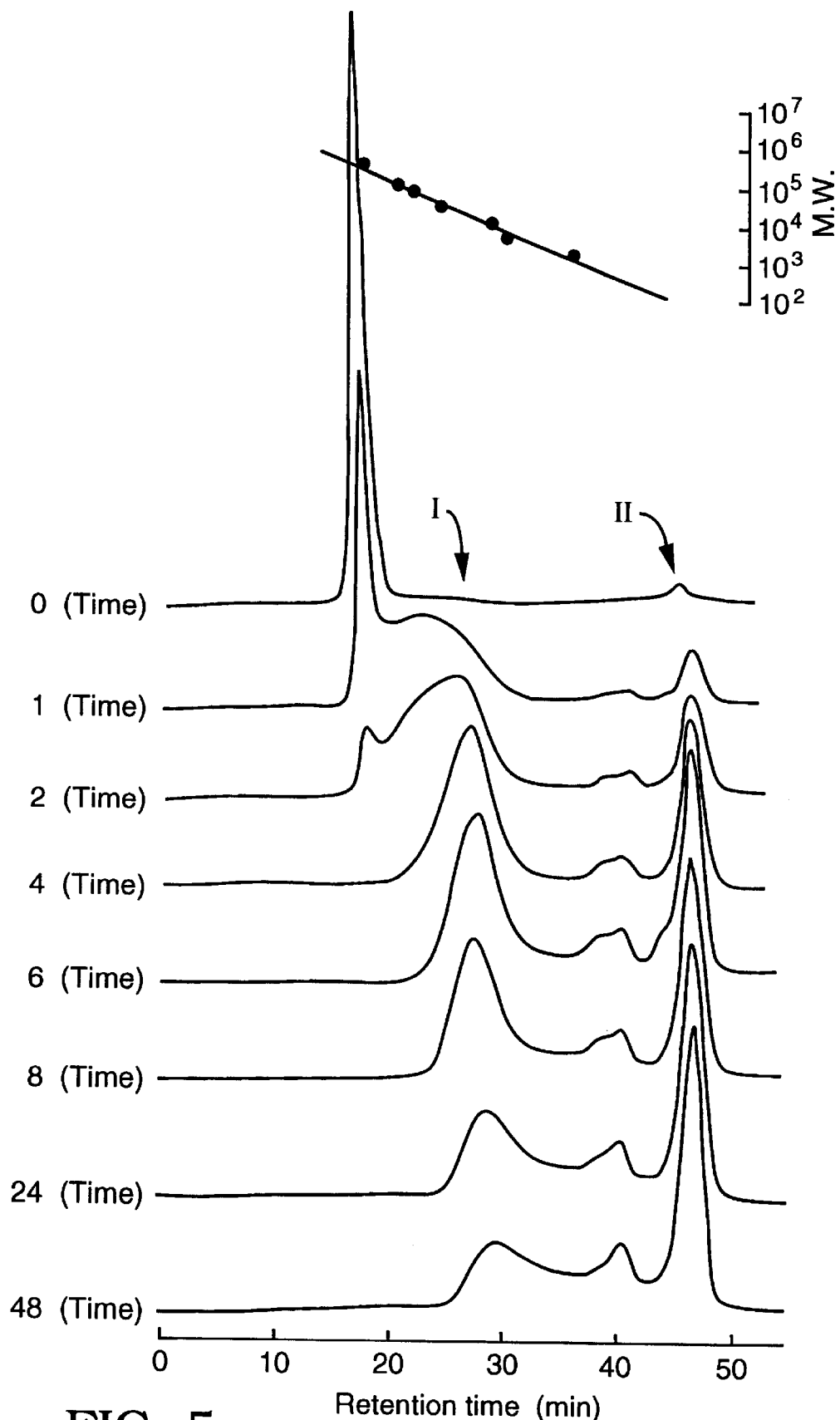
FIG. 5 is a diagram showing the change in elution pattern of gel filtration chromatography of products when CGTase is allowed act on amylopectin.
Figure 6:
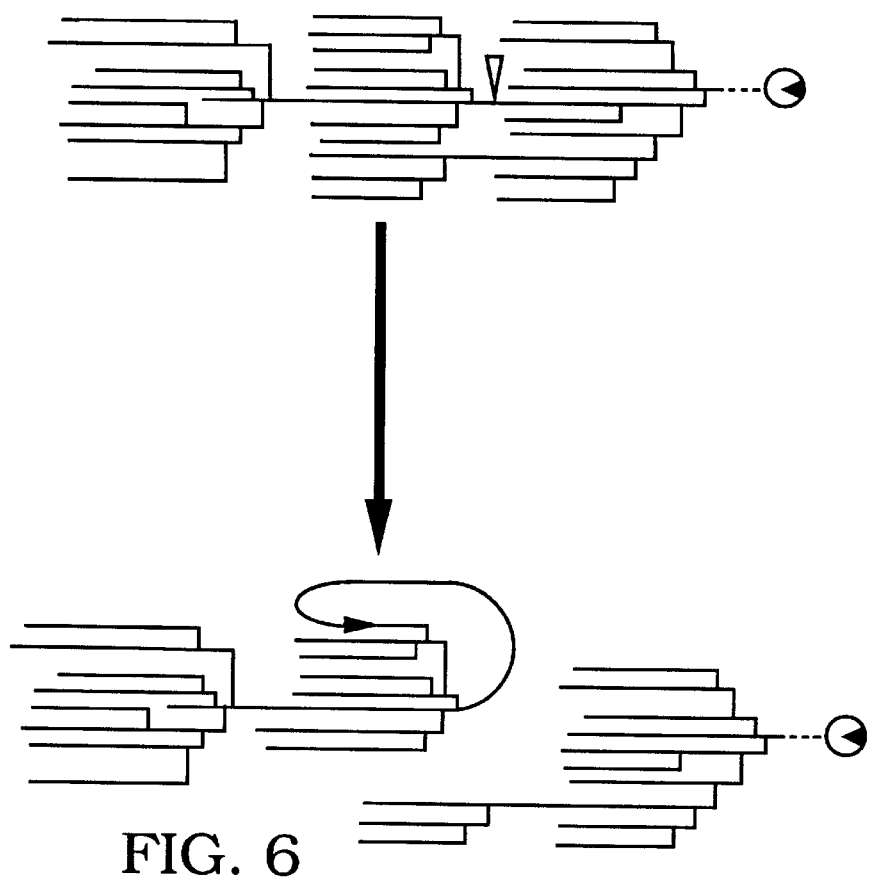
FIG. 6 is a diagram showing a novel action mechanism of CGTase.

On the other hand, the inventors of the present invention studied the change in elution pattern of gel filtration chromatography of a product obtained when CGTase is allowed to act on amylopectin. FIG. 5 shows the result. Amylopectin eluted in a void volume position was decomposed into low molecular weight molecules with the process of enzymatic reaction and 2 major low molecular Peaks I and II. Among these peaks, Peak II includes low molecular CD (α- and β-CD). Small peaks between Peaks I and II include mixture of large CDs with degrees of polymerization of about 9 to 14, inner branched CDs, outer branched CDs, and linear maltooligosaccharide. Peak I includes glucans having higher molecular weight than these CDs and lower molecular weight than amylopectin. These results cannot be explained by the mechanism of FIG. 4B, but can be explained by the reaction to form a larger cyclic structure (FIG. 6).

In the case where such cyclization reaction occurs, since the cyclic structure portion is not decomposed with glucoamylase, glucan exhibiting resistance to glucoamylase is supposed to be generated.

Figure 7:
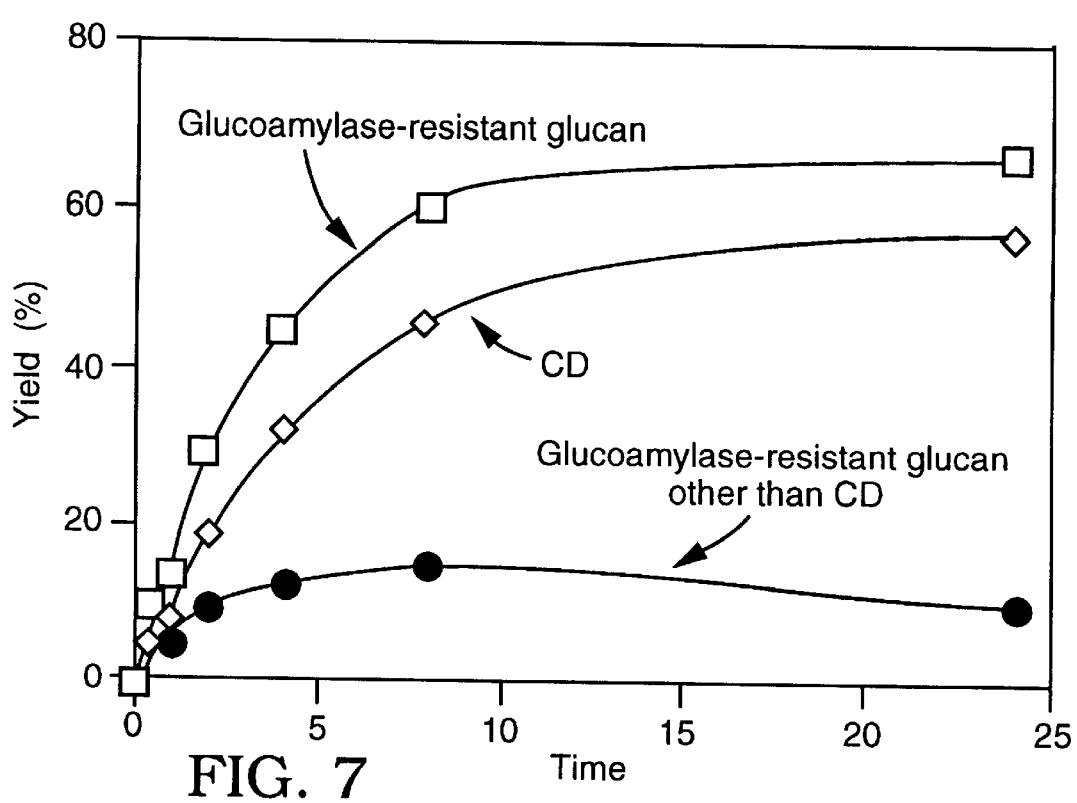
FIG. 7 is a graph showing that cyclic glucan other than CD is produced by the action of CGTase.

The amounts of CDs in the products and the amount of glucan resistant to glucoamylase other than CD at respective reaction times in FIG. 5 were measured. Herein, the amount of CD in the reaction solution is obtained by determining α, β, γ-CD by HPLC methods. The amount of glucan resistant to glucoamylase is obtained by measuring the amount of glucosyl units in the glucan which is not decomposed with glucoamylase. The amount of glucan resistant to glucoamylase other than CD is obtained by subtracting the amount of CD from the total amount of glucan resistant to glucoamylase. As shown in FIG. 7, it has been found that by allowing CGTase to act on amylopectin, glucan resistant to glucoamylase other than CD is clearly generated. Thus, it is considered that Peak I is formed by cyclization reaction to form larger cyclic structure than CD as shown in FIG. 6.

By fractionating and analyzing the product included in Peak I, it is confirmed that this product is glucan having a cyclic structure containing α-1,6-bonds. This shows that when CGTase is allowed to react with amylopectin, the CGTase catalyzes a cyclization reaction including α-1,6-bonds in addition to a CD synthesizing reaction.

As described above, the present invention is achieved by finding the ability of various enzymes acting on carbohydrate to form a cyclic structure. Thus, any enzyme having the ability of forming a cyclic structure is included in the present invention.

Branching Enzyme

Branching enzyme is present in various plants, animals and microorganisms such as bacteria. Its origin is not limited. Branching enzyme purified from *E. coli* having a plasmid encoding branching enzyme gene from thermophilic bacteria is preferred because of a high reaction optimum temperature, or branching enzyme derived from potato tuber is preferred because of facility in obtaining a great amount of enzyme.

D-enzyme

As D-enzyme, those derived from various plants or microorganisms can be used. D-enzyme was first found in potato; however, D-enzyme is known to be present in various plants and microorganisms such as *E. coli*. This enzyme is called D-enzyme in the case when it is derived from plants, and amylomaltase in the case when it is derived from microorganisms. Thus, the origin of D-enzyme is not limited, and those obtained by expressing gene encoding D-enzyme derived from plants in a host such as *E. coli* can be advantageously used.

CGTase

As CGTase, CGTase derived from well-known microorganisms or commercially available CGTase can be used. As CGTase derived from microorganisms, commercially available CGTase (Hayashibara Biochemical Research Institute Co., Ltd., Okayama) derived from *Bacillus stearothrmophilus*, CGTase (trade name: Contizyme, produced by Amano Seiyaku, Nagoya) derived from *Bacillus macerans*, or CGTase derived from *Alkalophilic Bacillus* sp. A2-5a can be preferably used. More preferably, CGTase derived from *Alkalophilic Bacillus* sp. A2-5a can be used. *Alkalophilic Bacillus* sp. A2-5a is a strain producing CGTase having high activity in an alkali region disclosed in Japanese Laid-Open Patent Publication No. 7-107972, and this strain was deposited by the Applicant in the Agency of Industrial Science and Technology, Biotechnology Industrial Research Institute and assigned accession No. FERM P-13864.

The above-mentioned branching enzyme, D-enzyme, or CGTase can be used for producing the glucan of the present invention, even though it is a crude enzyme used in purification, if the enzymatic activity of endo-type amylases hydrolyzing an α-1,4- or α-1,6-glucoside bond in a starch molecule is not detected or is very weak.

Furthermore, the enzyme used in the present invention can be used for reaction even if it is immobilized, irrespective of whether it is a purified enzyme or a crude enzyme. The reaction can be performed by a batch method or a continuous method. As a method for immobilizing enzyme, methods known to those skilled in the art, such as a carrier bond method (e.g., a covalent bond method, an ion bond method, and a physical adsorption method), a cross-linking method or an including method (of a lattice type or of a microcapsule type), or the like can be used.

Material to be used: Substrate

As a material used in the present invention, a carbohydrate having α-1,4-glucoside bonds and at least one α-1,6-glucoside bond can be used. Examples of the carbohydrate include starch, partially decomposed starch, amylopectin, glycogen, waxy starch, high-amylose starch, soluble starch, dextrin, starch hydrolysate, and enzymatically synthesized amylopectin with phosphorylase.

As the starch, any commercially available starch can be used. Examples of the starch include underground starch such as potato starch, sweet potato starch, arrowroot starch, and tapioca starch; and above-ground starch such as corn starch, wheat starch, and rice starch.

Examples of the partially decomposed starch include those obtained by partially hydrolyzing the above starch with enzyme or acid, and debranched starch.

As the amylopectin, waxy corn starch composed of 100% amylopectin is preferably used since the distribution of molecular weight of glucan to be produced becomes homogeneous. For example, amylopectin with a degree of polymerization of about 600 or more can be used as a material.

In the case of using branching enzyme, glucan having only α-1,4-bonds can also be used as a material. Examples of the glucan having only α-1,4-glucoside bonds include amylose, partially decomposed starch, debranched starch, enzymatically synthesized amylose with phosphorylase, and maltooligosaccharide. Amylose with a degree of polymerization of about 400 or more can be preferably used.

Furthermore, as a material, derivatives of the above-mentioned starch or partially decomposed starch can be used. Examples of the derivatives include those obtained by glycosylating, hydroxyalkylating, alkylating, acetylating, carboxymethylating, sulfurating, or phosphorylating at least one alcoholic hydroxyl group of the above-mentioned starch. Furthermore, mixtures of two or more kinds of these derivatives can also be used as a material.

Enzymatic Reaction on Material

Any steps of allowing the above-mentioned material to react with the above-mentioned enzyme can be used in the method for producing the glucan of the present invention, as long as the steps are conducted under conditions of pH, temperature, and the like allowing the glucan of the present invention to be generated. The concentration (substrate concentration) of the material can be determined considering the reaction conditions and the like.

In the case of using branching enzyme, the reaction pH is usually in the range of about 3 to about 11, preferably in the range of about 4 to about 10, and more preferably about 7 to about 9 in terms of reaction rate, efficiency, enzyme stability, and the like. The temperature is in the range of about 10° C. to about 110° C., preferably in the range of about 20° C. to about 90° C. in terms of reaction rate, efficiency, enzyme stability, and the like. The substrate concentration is usually in the range of about 0.05% to about 60% by weight, preferably in the range of about 0.1% to about 30% by weight in terms of reaction speed, efficiency, handling of an enzyme solution, and the like. The amount of enzyme to be used is usually in the range of 50 to 10,000 units per gram of substrate.

In the case of using D-enzyme, the reaction pH is usually in the range of about 3 to about 10, preferably in the range of about 4 to about 9, and more preferably about 6 to about 8 in terms of reaction rate, reaction efficiency, enzyme stability, and the like. The temperature is in the range of about 10° C. to about 90° C., preferably in the range of about 20° C. to about 60° C., and more preferably in the range of about 30° C. to about 40° C. in terms of reaction speed, reaction efficiency, enzyme stability, and the like. In the case of using enzyme obtained from thermophilic microorganisms, a high temperature in the range of about 50° C. to about 110° C. can be used. The concentration (substrate concentration) of a material can be determined considering the reaction conditions and the like. The concentration is usually in the range of about 0.1% to about 50% by weight, preferably in the range of about 0.1% to about 30% by weight in terms of reaction rate, efficiency, handling of a substrate solution, and the like, and more preferably in the range of about 0.1% to about 20% in terms of solubility and the like. The amount of enzyme to be used is determined by the relationship between the reaction time and the concentration of the substrate, and it is usually preferred to select the enzyme amount so as to allow the reaction to proceed to completion in about 1 to about 48 hours. The amount is usually in the range of about 500 to about 100,000 units per gram of a substrate, preferably in the range of about 700 to about 25,000 units per gram of a substrate, and most preferably in the range of about 2,000 to about 20,000 units per gram of a substrate.

In the case of using CGTase, the reaction pH is usually in the range of about 4 to about 11, preferably in the range of about 4.5 to about 10 and more preferably in the range of about 5 to about 8 in terms of reaction rate, efficiency, enzyme stability, and the like. The reaction temperature is in the range of about 20° C. to about 110° C., preferably in the range of about 40° C. to about 90° C. in terms of reaction speed, efficiency, enzyme stability, and the like. The substrate concentration is usually in the range of about 0.1% to about 50 wt %, preferably in the range of about 0.1% to about 30 wt % in terms of reaction speed, efficiency, handling of a substrate solution, and the like. The amount of enzyme to be used is usually in the range of about 1 to about 10,000 units per gram of a substrate, preferably in the range of about 1 to about 1,000 units per gram of a substrate, and most preferably in the range of about 1 to about 500 units per gram of substrate.

A method for determining the unit of each enzyme will be described in examples described later.

Isolation and Purification of Product

Various glucans having cyclic structures obtained in the above reaction can be separated by separation methods known to those skilled in the art such as chromatography (e.g., gel filtration chromatography, and HPLC), membrane filtration, and precipitation method using a solvent such as methanol and ethanol. One or more of the separating methods or purifying methods described above may be used.

According to the method of the present invention, the yield of the glucan from starch as a material is very high. In particular, when branching enzyme is used, the yield is almost 100%. In the case where D-enzyme or CGTase is used, glucan having only a cyclic structure is produced; however, this glucan can be easily separated from cyclic glucan having a branch structure of interest by separation methods mentioned above such as gel filtration using a Sephadex column.

The separated cyclic glucan can be separated in accordance with the molecular weight by gel filtration such as HPLC.

Reaction Product

Glucan produced by the method of the present invention has a degree of polymerization of 50 or more and has an inner branched cyclic structure portion and an outer branched structure portion. The glucan has a degree of polymerization preferably in the range of about 50 to about 10,000, more preferably in the range of about 50 to about 7,000, and most preferably in the range of about 50 to about 5,000.

The degree of polymerization of the inner branched cyclic structure of the glucan produced by the method of the present invention is preferably in the range of about 10 to about 500, more preferably in the range of about 10 to about 100.

The inner branched cyclic structure portion of the glucan produced by the method of the present invention has at least one α-1,6-glucoside bond, usually 1 to about 200, and preferably about 1 to about 50.

The degree of polymerization of the glucan of this invention can be measured by gel filtration chromatography using amylose, whose degree of polymerization is known, as a standard. Furthermore, by using a differential refractometer and a low angle laser light scattering photometer, the degree of polymerization can be determined by the following principle. The output of the differential refractometer is proportional to the concentration of glucan, and the output of the low angle laser light scattering photometer is proportional to both of the degree of polymerization and the concentration of the glucan. Thus, by measuring the ratio of the outputs of both detectors, the degree of polymerization of glucan can be determined.

Evidence that the Glucan has a Cyclic Structure

It can be confirmed by using glucoamylase whether or not the glucan obtained by the method of the present invention has an inner branched cyclic structure.

Figure 8:
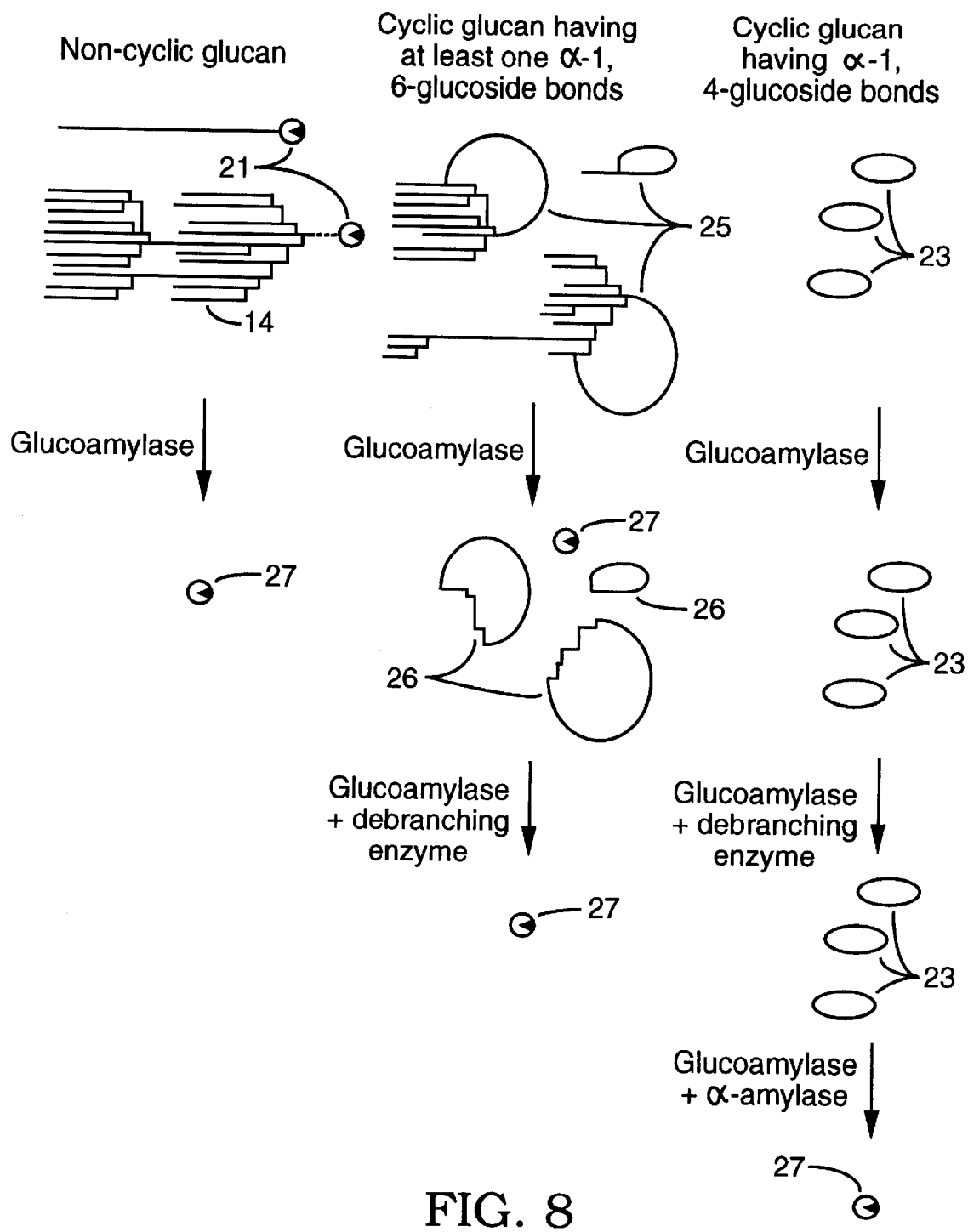
FIG. 8 is a schematic diagram illustrating the decomposition of glucan by each enzyme, for determining the structure of glucan obtained by the method of the present invention.

Exo-glucoamylase is an enzyme that successively hydrolyzes α-1,4-glucoside bonds from a non-reducing end of glucan such as starch. It is known that exoglucoamylase is capable of hydrolyzing α-1,6-glucoside bonds from a non-reducing end at low speed. As shown in FIG. 8, amylose or amylopectin having no cyclic structure can be completely decomposed into glucoses 27 with exo-type glucoamylase. However, in glucans 25 and 23 having a cyclic structure in its molecule, only non-cyclic structure portion is decomposed, and their cyclic structure portion remains as material which is not decomposed with glucoamylase (hereinafter, referred to as glucoamylase-resistant component).

Whether or not this glucoamylase-resistant component (cyclic structure portion) has an inner branched structure can be determined by its sensitivity with respect to the debranching enzyme cleaving an α-1,6-bond. The cyclic glucan 26 having an inner branched cyclic structure (α-1,6-glucoside bond) can be completely decomposed into glucose 27 by combined use of debranching enzyme and glucoamylase.

On the other hand, the glucan 23 having a cyclic structure with no inner branched cyclic structure (i.e. having only α-1,4-glucoside bonds) cannot be decomposed with debranching enzyme and exo-type glucoamylase. The cyclic glucan 23 can be completely decomposed into glucose by combined use of endo-type α-amylase and glucoamylase.

By utilizing the above-mentioned characteristics, the inner branched cyclic structure portion of glucan, the outer branched (non-reducing) structure portion thereof, and the cyclic structure portion thereof having only α-1,4-glucoside bonds can be quantitated.

It can be confirmed by the following (1) to (6) characteristics that the glucan produced according to the present invention has an inner branched cyclic structure.

(1) The number of reducing ends does not increase, compared with a raw material (starch etc.). That is, a reducing end cannot be detected. The number of reducing ends can be determined by the modified Park-Johnson method of Hizukuri et al., Carbohydr. Res. 94:205–213 (1981).

(2) When glucoamylase is allowed to act on the glucan, a glucoamylase-resistant component remains. This component is not decomposed by glucoamylase, even after phosphatase treatment. (3) The glucoamylase-resistant component is decomposed with isoamylase (produced by Hayashibara Biochemical Research Institute Co., Ltd., Okayama) hydrolyzing an α-1,6-glucoside bond in starch and becomes sensitive to the action of glucoamylase.

(4) The glucoamylase-resistant component is decomposed with endo-type α-amylase (produced by Nagase Seikagaku Kogyo Co., Ltd.), which hydrolyzes α-1,4-glucoside bonds in starch, and becomes sensitive to the action of glucoamylase.

(5) As a result of hydrolysis by endo-type α-amylase, isomaltosylmaltose (IMM) is generated. This agrees with the description that the minimum limit dextrin in the case where endo-type α-amylase is allowed to act on glucan having an α-1,6-glucoside bond is IMM (T. Yamamoto, Handbook of amylase and related enzymes, Pergamon Press, pp. 40–45 (1988)).

(6) The analysis of the molecular weight of the glucoamylase-resistant component by a laser ionization TOF-MS apparatus (manufactured by Shimazu Co., Ltd.) shows that the obtained value of the molecular weight coincides with the theoretical value of cyclic glucan and does not coincide with the theoretical value of noncyclic glucan.

The detection of the glucoamylase-resistant component used for confirming the presence of an inner branched cyclic structure portion can be conducted as follows. For example, glucoamylase is added to the glucan generated by the above reaction, and the mixture thus obtained is allowed to react at about 40° C. overnight. The reaction product is heated at 100° C. for 10 minutes and an insoluble substance is removed by centrifugation. Then, 10-fold volume of ethanol is added to the supernatant and the polysaccharide remained in the supernatant is collected as a precipitate. This process is repeated again to obtain glucoamylase-resistant component. It is noted that a short period of time (e.g., 1 to 2 hours) is enough for the second glucoamylase treatment.

In the case where a raw material, such as starch, used in the present invention is partially modified with a phosphate group, pretreatment is required for the detection of the glucoamylase-resistant component. For example, a reaction product is dissolved in a 10 mM carbonate buffer (pH 9.4) containing 10 mM of $MgCl_2$ and 0.3 mM of $ZnCl_2$, and phosphatase is added to the resultant solution. Thereafter, 10-fold volume of ethanol is added to the reaction mixture and a precipitate is collected. A glucoamylase-resistant component can be obtained by applying the above-mentioned method to this precipitation.

The degree of polymerization and the structure of the glucoamylase-resistant component can be determined by analyzing carbohydrates generated by a reaction of glucoamylase-resistant component with glucan hydrolases, as described in the above-mentioned points (1) to (6). Examples of the hydrolases include glucoamylase, a combination of glucoamylase and isoamylase, and a combination of glucoamylase and α-amylase. The reaction is conducted as follows. The glucoamylase-resistant component is dissolved in distilled water so as to obtain a concentration of 0.2% (w/v), and the above-mentioned hydrolases were respectively added in an appropriate amount to the resultant solution. The solution is allowed to react at 30 to 45° C. for an appropriate period of time (e.g., 1 hour). The decomposed glucoamylase-resistant component is subjected to a sugar analysis system (liquid transfer system: DX300, detector: PAD-2, column: Carbo Pac PA100, manufactured by Dionex) so as to be analyzed. The elution is conducted under the condition of, for example, a flow speed of 1 ml/minute, an NaOH concentration of 150 mM, a sodium acetate concentration of 0 minute-50 mM, 2 minutes-50 mM, 37 minutes-350 mM, 45 minutes-850 mM, and 47 minutes-850 mM. The degree of polymerization of the glucoamylase-resistant component and sugar generated by decomposition can be determined using this analysis.

Regulation of Degree of Polymerization

The degree of polymerization of glucan having an inner branched cyclic structure portion and an outer branched structure portion obtained by the method of the present invention can be regulated. For example, exotype amylase, for example, glucoamylase is allowed to act on the obtained glucan so as to cleave a sugar chain of the outer branched structure portion, thereby obtaining glucan having a lower degree of polymerization. This method is also included in the present invention.

Uses of Glucan of the Present Invention

The glucan of the present invention and the glucan obtained by the method of the present invention can be used for various uses of starch. In particular, they can be used as a composition for foods and drinks, a composition for food additives, a composition for an infusion, a composition for an adhesive, and an anti-retrogradation agent. In these uses, the glucan of the present invention can be used at a concentration appropriate for the respective uses.

Hereinafter, the present invention will be described by way of illustrative examples; however, the present invention is not limited by the examples.

EXAMPLES

A. Preparation of enzyme to be used and measurement of enzymatic activity

A-1: Preparation of branching enzyme: Preparation from potato and measurement of enzymatic activity Potato tuber was homogenized in 20 mM Tris-HCl (pH 7.5) buffer containing 5 mM of 2-mercaptoethanol (buffer A) and centrifuged. The resulting solution was applied to Q-Sepharose column after being passed through a filter with a pore diameter of 0.45 $\mu$m. The column was washed with a buffer containing 150 mM of NaCl in buffer A. Then, branching enzyme was eluted with a buffer containing 450 mM of NaCl in buffer A. Then, ammonium sulfate was added to the elute so as to obtain a final concentration of 500 mM. The mixture was applied to Phenyl Toyopearl 650M (produced by Tosoh Corporation) column which was washed by a buffer containing 500 mM of ammonium sulphate in buffer A. By changing the concentration of ammonium sulphate in buffer A from 500 mM to 0 mM, elution was conducted. Fractions including branching enzyme were collected and dialyzed against buffer A. Dialyzate was applied to PL-SAX column (produced by Polymer Laboratory (U.K.)) equilibrated with buffer A and eluted by changing the concentration of NaCl in buffer A from 150 mM to 400 mM to collect fractions including branching enzyme.

The enzymatic activity was determined as follows. A 100 $\mu$l of a reaction solution containing 5 mM of TrisHCl (pH 7.5), 0.05% (w/v) amylose, and enzyme was incubated at 30° C. for 30 minutes, and the reaction was terminated by adding 2 ml of an iodine solution (containing 1 mg/ml of KI, 0.1 mg/ml of $I_2$, and 3.8 mM of HCl), and the absorbance of the solution at a wavelength of 660 nm was measured. The amount of enzyme decreasing the absorbance by 1% per minute is defined as 1 unit.

A-2: Preparation of branching enzyme-2: Preparation of recombinant branching enzyme from *E. coli*

*Bacillus stearothermophilus* TRBE 14 strain (Agency of Industrial Science and Technology, Biotechnology Industrial Research Institute; Accession No. FERM P-13916) was used to obtain a donor of branching enzyme gene.

*Bacillus stearothermophilus* TRBE 14 strain was cultured in 500 ml flask containing 100 ml of L-culture medium at 50° C. overnight. After the completion of culture, the cells were collected by centrifugation. Chromosomal DNA was prepared from these collected cells by a phenol method (Saitoh and Miura, Biochimica et Biophysica Acta, 72, 619 (1963)). The chromosomal DNA thus obtained was partially degraded with restriction enzyme Sau3AI and subjected to NaCl density gradient centrifugation to collect DNA fragments of 10 kb or more. The collected DNA fragments of 10 kb or more were ligated with λ-EMBL3 vector (produced by Stratagene) previously cleaved with BamHI, using T4DNA ligase. A recombinant $\mu$-phage suspension containing thus ligated DNA was prepared by using an in vitro package kit (Stratagene).

*E. coli* P2392 was incubated by shaker in an NZY-culture medium (1% NZ amine, 0.5% yeast extract, and 0.5% NaCl) supplemented with 10 mM of $MgCl_2$ at 37° C. overnight. After incubation, cells were collected, suspended in 10 ml of 10 mM $MgCl_2$, and mixed with the recombinant λ-phage suspension. The mixture was kept warm at 37° C. for 20 minutes. Then, the mixture was placed on an NZY agar culture medium and kept warm at 37° C. overnight to obtain a plate with plaques.

A probe for selecting phage having a gene of interest from the recombinant λ-phage was prepared. In amino acid sequences of several kinds of branching enzymes, 4 conserved regions (Conserved Regions 1, 2, 3, and 4) which have already been found in α-amylase or the like are known to be present (J. Biol. Chem., 267, 18447 (1992)). Two kinds of DNA primers, a sequence (5'GAYTGGGTNCCNGSNCAYTTY 3': SEQ ID NO: 1) corresponding to a sequence of Conserved Region 1 shown in FIG. 9 and a sequence (3'WSNGTRCTRCTYCANCANGTR 5': SEQ ID NO: 2) corresponding to a sequence in the vicinity of Conserved Region 4 were synthesized. These synthetic primers were allowed to react with the chromosomal DNA of 10 kb or more obtained in the above, using Tth DNA polymerase (produced by Toyobo Co., Ltd.), whereby a DNA fragment sandwiched by the two synthetic primers was amplified. The reaction was repeated for 30 cycles, each cycle including 94° C. for 1 minute; 45° C. for 1 minute; and 72° C. for 1 minute. The amplified DNA fragment was about 560 bp. The amplified DNA fragment was ligated with pUC19 treated with restriction enzyme SmaI to obtain recombinant plasmid pTBE3. A radio-labelled probe for isolating branching enzyme gene was prepared from the recombinant plasmid pTBE3 by using a DNA labelling kit for multiprime method (Pharmacia).

A nylon filter (Amersham Corp.) was attached to the plate with plaques of the recombinant λ-phage. The plate was alkali-treated to denature the recombinant λ-phage DNA in the plaques, whereby the DNA was immobilized on the filter. The resultant filter was soaked in the solution of radio-labelled probe prepared in the above and hybridization was done at 65° C. for 16 hours. The filter was thoroughly washed, dried, and attached to an X-ray film so as to select recombinant λ-phage containing branching enzyme genes. The recombinant λ-phage thus obtained was named λ-TBE102. FIG. 10 shows a restriction enzyme map of λ-TBE102.

Figure 11:
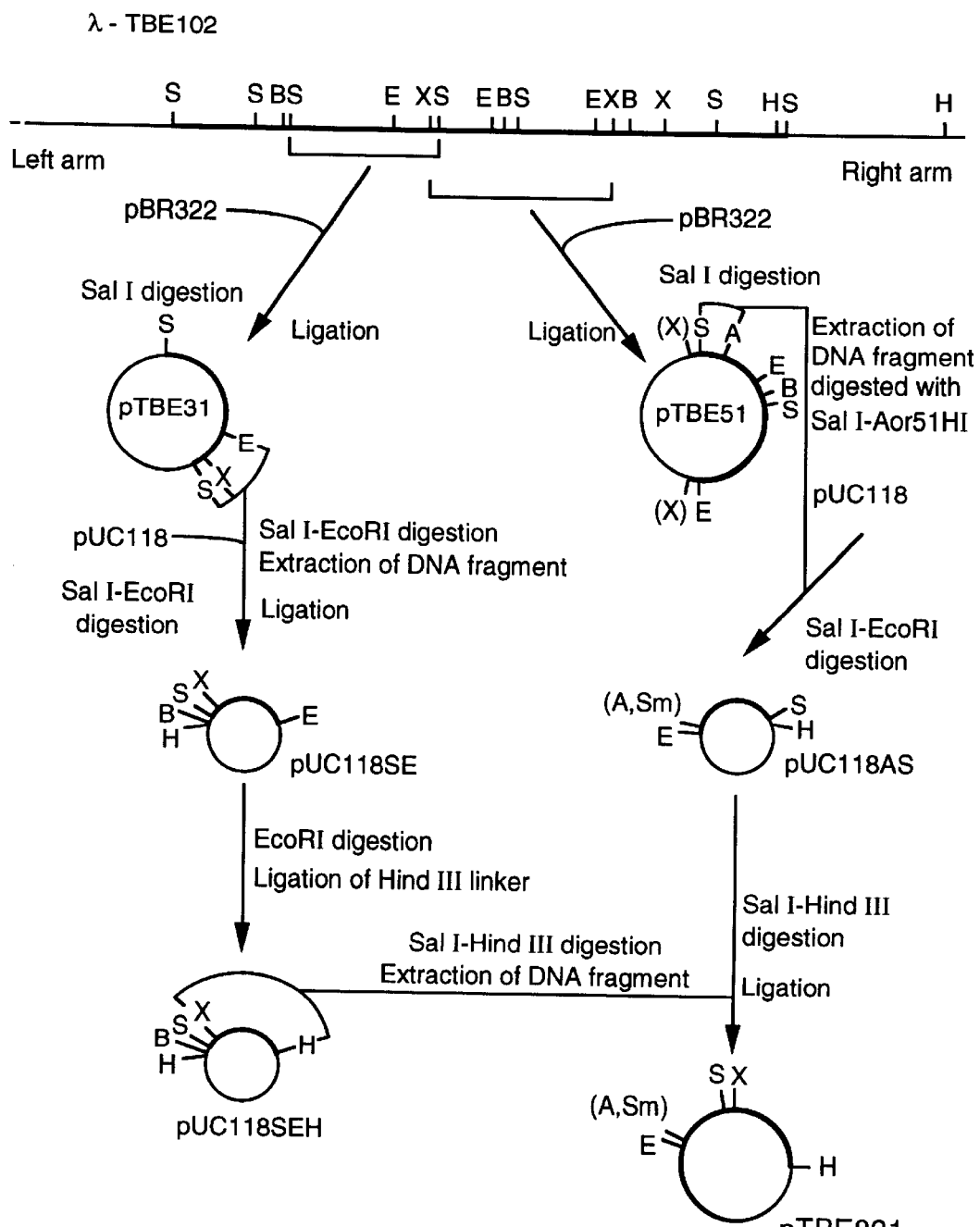
FIG. 11 is a diagram illustrating a method for constructing a plasmid containing branching enzyme gene.

A plasmid containing branching enzyme gene was produced by a method shown in FIG. 11. First, a DNA fraction was recovered from λ-TBE102, cleaved with SalI, and subjected to agarose gel electrophoresis. The DNA was transferred to a nitrocellulose filter by a conventional method and hybridized at 65° C. for 16 hours, using the above-mentioned probe. A 4 kb SalI fragment was hybridized. The 4 kb SalI fragment was isolated and introduced into an SalI site of pBR322 to produce pTBE31.

Next, 1.4 kb of a SalI-EcoRI fragment was isolated from pTBE31 and was ligated to plasmid pUC118 treated with SalI-EcoRI to prepare pUC118SE. pUC118SE was cleaved with EcoRI and cleaved sites were made blunt ends with T4DNA polymerase. Hind III linker was introduced into the cleaved sites to form pUC118SEH.

On the other hand, about 5 kb of a XhoI DNA fragment containing the above 4 kb SalI fragment was introduced into SalI site of pBR322 to form pTBE51. A SalI-Aor51HI DNA fragment was cut out from pTEB51 and ligated to pUC118 cleaved with SmaI-SalI to form pUC118AS.

About 1 kb of BamHI-SalI DNA fragment was isolated from pUC118AS and ligated to pUC118SEH treated with BamHI-SalI to form pTBE821. This plasmid pTBE821 encoded an amino acid sequence (SEQ ID NO: 3) of branching enzyme.

This plasmid pTBE821 was introduced into *E. coli* TG-1 by a conventional method. *E. coli* TG-1 was cultured and centrifuged at 8,000 rpm for 5 minutes to obtain cells. These cells were suspended in 50 mM of Tris-HCl (pH 7.0) containing 5 mM of 2-mercaptoethanol (buffer B) and disrupted with sonication. Undissolved substance was removed by centrifugation at 12,000 for 10 minutes, the suspension was heated at 60° C. for 15 minutes and precipitates such as denatured protein was removed by centrifugation at 12,000 rpm for 10 minutes. The supernatant thus obtained was dialyzed against buffer B and then applied to Q-Sepharose column (manufactured by Pharmacia). The column was washed with a buffer containing 100 mM of NaCl in buffer B. Branching enzyme was eluted with a buffer containing 200 mM of NaCl in buffer B. Then, ammonium sulfate was added to the eluate so as to obtain a final concentration of 170 mM. The mixture was applied to Phenyl Toyopearl 650M (Tosoh Corporation) column and branching enzyme was eluted with buffer B to obtain branching enzyme.

The measurement of the enzymatic activity was conducted in the same way as in the case of potato branching enzyme, except that the reaction temperature was 50° C.

A-3: Preparation of D-enzyme and measurement of enzymatic activity

D-enzyme was purified by the method described in Takaha et al., J. Biol. Chem., vol. 268, pp. 1391–1396 (1993). First, potato tuber was homogenized in buffer A and centrifuged. The resultant solution was applied to a Q-Sepharose column (16×100 mm Pharmacia) after being passed through a membrane having pores of 0.4 μm. The column was washed with the buffer containing 150 mM of NaCl in buffer A. D-enzyme was eluted with a buffer containing 450 mM of NaCl in buffer A. After elution, the eluate was dialyzed against buffer A and ammonium sulfate was added to the dialyzate so as to obtain a final concentration of 500 mM. This solution was loaded onto a Phenyl Toyopearl 650M (Tosoh Corporation) column (10×100 mm), and the elution was conducted by changing the concentration of ammonium sulfate in buffer A from 500 mM to 0 mM. Active fractions of D-enzyme were collected and dialyzed against buffer A. Dialysate was concentrated by an Amicon Centricon 30 microconcentrator, and the concentrated dialysate was applied to PL-SAX HPLC column (Polymer Laboratory U.K.) and eluted in a 150 to 400 mM of NaCl linear concentration gradient in buffer A. Active fractions were collected from the eluate thus obtained and concentrated by the above-mentioned Amicon Centricon 30 microconcentrator.

The measurement of the enzymatic activity was determined by a method using glucose oxidase (Barham et al., (1972) Analyst 97:142). According to this method, 100 μl of a reaction mixture containing 100 mM of TrisHCl (pH 7.0), 5 mM of 2-mercaptoethanol, 1% (W/V) of maltotriose, and enzyme was allowed to react at 37° C. for 10 minutes. The reaction solution was heated for 3 minutes in boiling water to stop the reaction. Glucose liberated by the reaction was measured. The amount of enzyme used for generating 1 μmol of glucose per minute is defined as 1 unit.

A-4: Preparation of CGTase

CGTase derived from Alkalophilic Bacillus sp. A2-5a (hereinafter, referred to as A2-5a strain) was used. Japanese Laid-Open Patent Publication No. 7-107972 discloses the properties of a CGTase producer Alkalophilic Bacillus sp. A2-5a, which was deposited by the Applicant in the Agency of Industrial Science and Technology, Biotechnology Industrial Research Institute and assigned accession No. FERM P-13864.

A method for purifying CGTase derived from an A2-5a strain was as follows:

The A2-5a strain was cultured in an AL liquid culture medium (1% soluble starch, 4% corn steep liquor, 0.1% $K_2HPO_4$, 0.02% $MgSO_4$, $7H_2O$, 1% $Na_2CO_3$, pH=10.0) at 33° C. for 24 hours. After incubation, culture broth was centrifuged to remove cells therefrom and the culture supernatant thus obtained was collected. Twenty grams of starch was added to 1.6 L of the culture supernatant, the mixture was stirred at 4° C. for 16 hours, and CGTase was allowed to adsorb to starch granule. CGTase absorbed to starch particles was applied to a column, and the column was washed 5 times with 100 ml of 22.8% ammonium sulfate solution. Thereafter, CGTase was eluted 5 times with 100 ml of 33 mM $Na_2HPO_4$. Ammonium sulfate was added to the eluate so as to obtain a final concentration of 57%. The precipitate thus obtained was collected and dialyzed against 20 mM of Tris-hydrochloride buffer (pH 7.5). The entire solution thus obtained was loaded onto a Q-Sepharose column (8 ml) pre-equilibrated with 20 mM of Tris-hydrochloride buffer (pH 7.5), and the column was washed with 50 ml of Tris-hydrochloride buffer containing 0.4M of NaCl. By changing the concentration of NaCl in the buffer from 0.4M to 1M, CGTase was eluted. Then, active fractions of CGTase were collected to obtain purified CGTase derived from the A2-5a strain.

A-5: Preparation of immobilized CGTase

One g of carrier Quitopal BCW-3503 (Fuji Spinning Co., Ltd.), washed with distilled water, for immobilization of enzyme and 5 ml of 20 mM of sodium acetate buffer (pH 5.5) containing 100 units of CGTase was incubated with gentle stirring at room temperature for 2 hours, whereby CGTase was adsorbed to the carrier. The suspension was filtrated and the CGTase activity of the filtrate was measured. The CGTase activity was hardly detected. Therefore, it was considered that most of the CGTase was bound to the carrier. This CGTase-bound carrier was used for reaction.

The CGTase activity was measured as follows: 1.5% soluble starch solution (adjusted to pH 5.5 with 20 mM of sodium acetate buffer) was placed in a constant temperature bath previously set at 40° C. Then, CGTase was added to this starch solution. After 10 minute, 0.5 ml of solution containing 0.5N acetic acid-0.5N HCl (5:1 v/v) was added to the reaction solution (0.25 ml) to stop the reaction. Then, 0.1 ml of the solution was taken and a solution containing 0.005% $I_2$ and 0.05% KI was added thereto. The resultant solution was stirred and allowed to stand at room temperature for 20 minutes. The absorbance of this solution at 660 nm was measured. At this time, a solution with no CGTase added was prepared as a blank, and the same procedure was conducted. Under this condition, the amount of enzyme causing the decrease in absorbance by 10% per minute at 660 nm was determined to be one unit.

B. Production of glucan using branching enzyme

Example 1: Preparation of Glucan

Five grams of commercially available waxy corn starch (having an average degree of polymerization of 30,000 or more) was suspended in 40 ml of 5 mM sodium phosphate buffer (pH 7.5), and the suspension was gelatinized in a hot bath at 100° C., followed by being cooled to about 50° C. Then, 2000 units of purified, recombinant branching enzyme were added to this gelatinized solution and allowed to react 50° C. for 6 hours.

The reaction solution was heated at 100° C. for 20 minutes, and denatured enzyme protein was removed therefrom by centrifugation at 10,000 rpm for 15 minutes. Twice volume of ethanol was added to the supernatant, and the mixture was allowed to precipitate. The precipitate was lyophilized to obtain about 4.8 g of powdery glucan.

Example 2: Measurement of Degree of Polymerization

The degree of polymerization was measured by gel chromatography, using a differential refractometer and a low angle laser light scattering photometer. The glucan obtained in the above reaction was dissolved so as to be 0.6% (W/V) in 0.1M phosphate buffer (pH 6.2) containing 1.5% acetonitrile and 0.02% sodium azide. Then, 200 µl of this solution was applied to a column obtained by connecting Asahipak GS520, Asahipak GS320 (both manufactured by Asahi Chemical Industry Co., Ltd.), and TSK-G2000PW (Tosoh Corporation).

Figure 12:
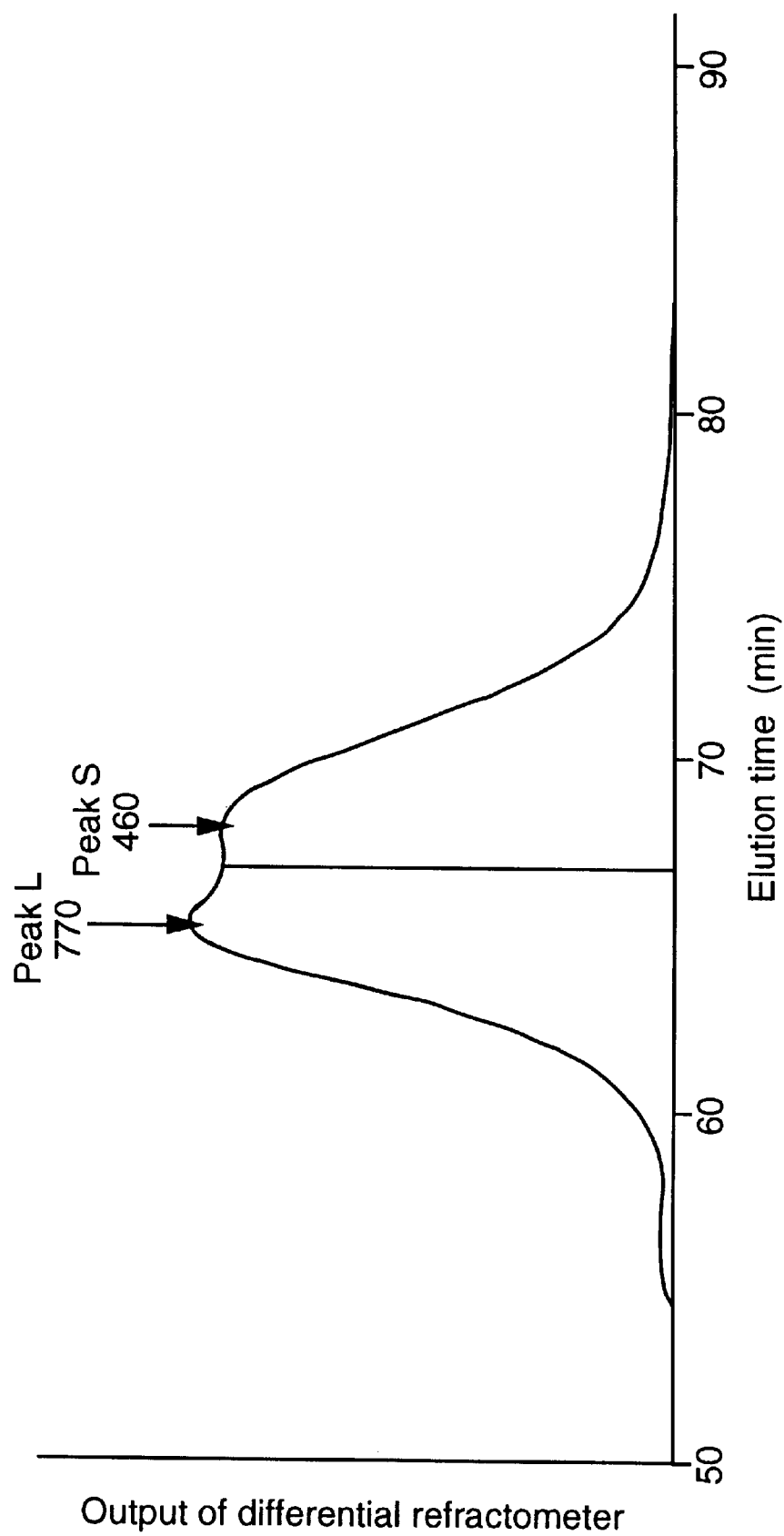
FIG. 12 is an elution pattern of glucan prepared in Example 1 on gel filtration column.

FIG. 12 shows an elution pattern. As shown in FIG. 12, the degree of polymerization of glucan thus produced was in the range of about 50 to 5,000, and peaks S and L were found at 460 and 770, respectively. The weight average degree of polymerization was 900.

Example 3: Determination of Structure of Glucan Obtained in Example 1

3-1: Quantitation of reducing end

The quantitation of reducing end of glucan obtained in Example 1 was conducted by the modified Park-Johnson method of Hizukuri et al. Compared with the waxy corn starch as a raw material, the increase in the number of reducing ends was not detected. Since the degradation of the material into lower molecules without increasing reducing ends can only be explained by the cyclizing reaction, it is concluded that the glucan has one cyclic structure in its molecule.

3-2: Obtaining glucoamylase-resistant component

The detection of glucoamylase-resistant component was conducted as follows:

First, 500 mg of the glucan obtained in Example 1 was thoroughly dissolved in 500 µl of DMSO. To this glucan solution, 500 µl of 1M sodium acetate buffer (pH 5.5), 3 ml of distilled water, and 1 ml of 50 units/ml glucoamylase were added, and the mixture was reacted at 40° C. for 3 hours. The reaction mixture was heated at 100° C. for 10 minutes, and undissolved substance was removed therefrom by centrifugation at 10,000 rpm for 15 minutes. Then, 10-fold volume of ethanol was added to the supernatant, and the mixture was centrifuged at 10,000 rpm for 15 minutes to collect a precipitate. The precipitate thus obtained was dried and dissolved in 1 ml of distilled water. Fifty units of glucoamylase were added to the solution thus obtained, followed by being reacted at 40° C. for 3 hours. The reaction solution was heated at 100° C. for 10 hinutes, and undissolved substance was removed by centrifugation at 10,000 rpm for 15 minutes. Then, 10-fold volume of ethanol was added to the supernatant, and the mixture was centrifuged to collect a precipitate. The precipitate thus obtained was dried to obtain 13 mg of powdery glucoamylase-resistant component. This suggested that the glucan obtained in Example 1 had a cyclic structure.

Figure 13:
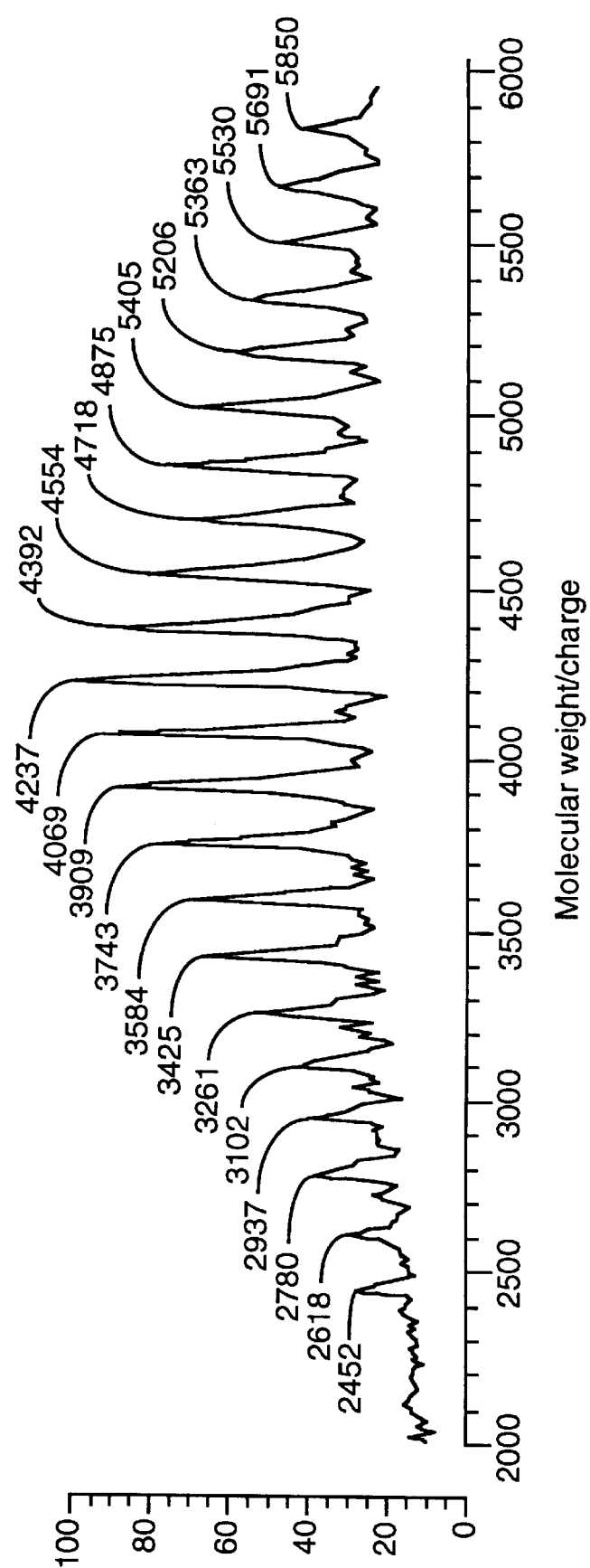
FIG. 13 is a diagram showing the result of measurement of molecular weight of a glucoamylase-resistant component.

3-3: Measurement of degree of polymerization of glucoamylase-resistant component The glucoamylase-resistant component thus obtained was subjected to gel filtration chromatography using a differential refractometer and a low angle laser light scattering photometer to obtain an average degree of polymerization of 49. This value was smaller than the average degree of polymerization of 900 of the glucan before being decomposed, indicating that an outer branched structure portion degradable with glucoamylase was present. From this glucoamylase-resistant component, low molecule portions were obtained by gel filtration chromatography. The low molecule portions were subjected to laser ionization TOF-MS apparatus (Kompact Maldi, manufactured by Shimadzu Corporation). As shown in FIG. 13, many peaks were observed. The molecular weight of these portions was well matched with the theoretical value of glucans having cyclic structures, each having a degree of polymerization different from each other by one. An error was within the limits (±0.2%) of the apparatus; the error was not matched with the theoretical value of glucan not having a cyclic structure. In FIG. 13, the molecular weight at the lowest peak is 2455, which is matched with the molecular weight of cyclic glucan with a degree of polymerization of 15 with a sodium ion added. In addition, a peak at which the molecular weight was matched with that of cyclic glucan with a degree of polymerization of 16 to 36 was detected.

3-4: Digestion of glucoamylase-resistant component with various kinds of amylases The glucoamylase-resistant component obtained in the above was dissolved in distilled water so as to be 0.4% (w/v). Then, amylases shown in FIG. 14 were respectively added to 50 µl of the solution so as to be 60 µl with a concentration shown in FIG. 14. The resulting solutions were allowed to react at 40° C. overnight. The reaction solutions were heated at 100° C. for 5 minutes, and denatured protein was removed by centrifugation at 12,000 for 5 minutes. Each of the reaction products was subjected to a carbohydrate analysis system of Dionex. The conditions described previously were used.

Figure 14:
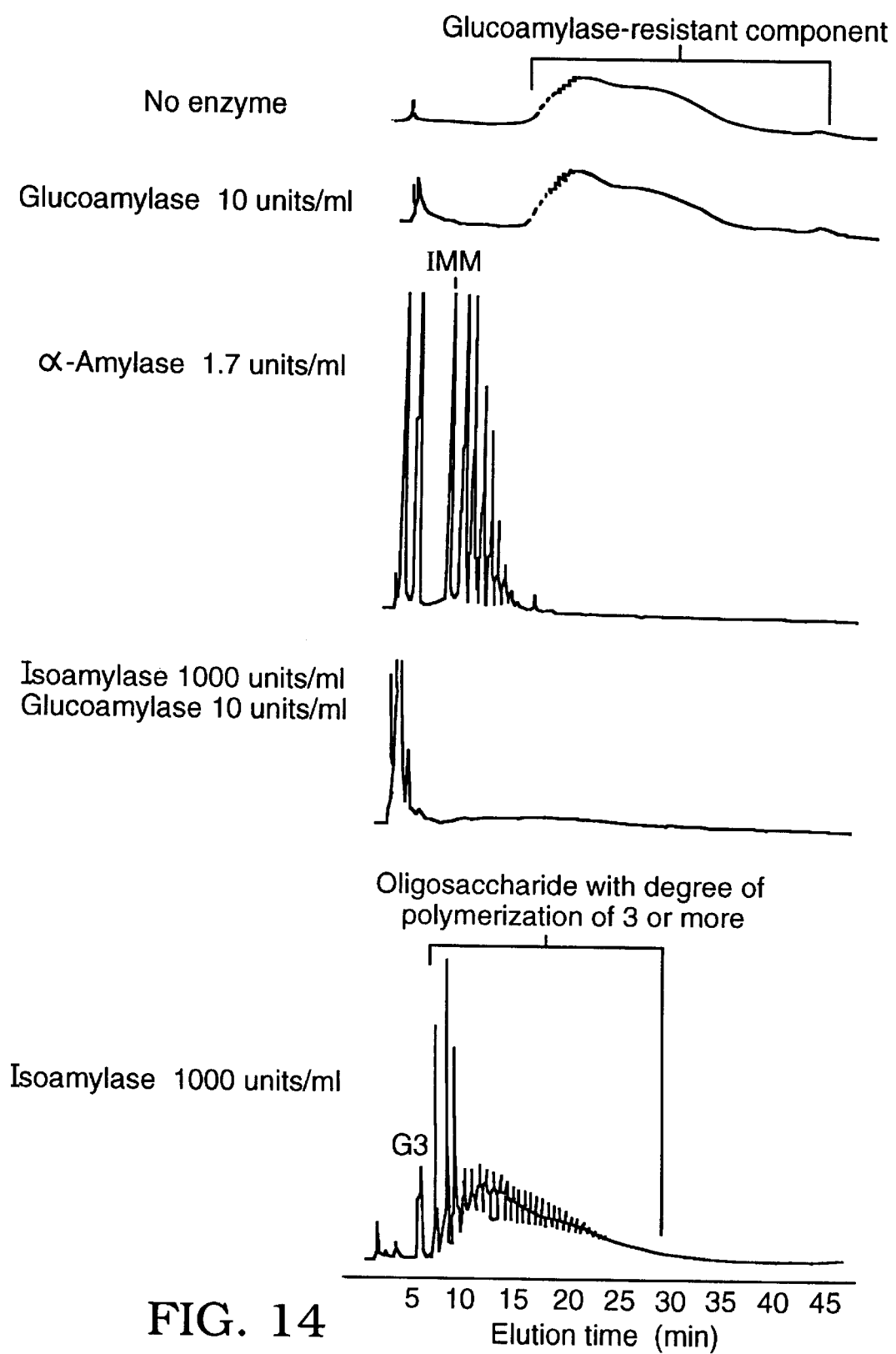
FIG. 14 shows carbohydrate generated by the digestion of the glucoamylase-resistant component with various kinds of amylases.

As shown in FIG. 14, the glucoamylase-resistant component was not decomposed with single use of glucoamylase; however, it was decomposed with α-amylase (Nagase Biochemical Industrial Co., Ltd.), i.e., endotype amylase hydrolyzing α-1,4-glucoside bonds in a starch molecule, and IMM was detected. The glucoamylase-resistant component was also decomposed by the combined use of glucoamylase and isoamylase (Hayashibara Biochemical Research Institute) hydrolyzing α-1,6-glucoside bond in starch. Furthermore, as shown in FIG. 14, the glucoamylase-resistant component was partially decomposed with the single use of isoamylase and generated oligosaccharide with a degree of polymerization of 3 or more.

Under the circumstances described above, the glucoamylase-resistant component thus obtained was found to be cyclic glucan and to include at least one α-1,6-glucoside bond.

3-5: Structure of glucan obtained in Example 1

As evidence for the presence of an outer branched structure in the glucan obtained in Example 1, it was confirmed that glucosyl stubs were present in the glucoamylase-resistant component. Herein, the glucosyl stub refers to a glucose residue of a bound portion between an outer branched structure portion and a cyclic portion, which remains when the glucoamylase-resistant component is treated with glucoamylase. By determining non-reducing ends of the glucoamylase-resistant component by a rapid Smith degradation method described in Hizukuri et al. (1978) Carbohydr. Res: 63: 261–264, 19% of the entire glycosyl groups of the glucoamylase-resistant component were a glucosyl stub bound to a cyclic structure. Thus, it was considered that about 9 glucoses of the glucoamylase-resistant component (cyclic structure) having an average degree of polymerization of 49 were glucosyl stubs derived from the outer branched structure, and the remaining 40 glucoses formed an inner branched cyclic structure.

From the above, the glucan obtained in Example 1 was found to have a plurality of outer branched structures portions in addition to an inner branched cyclic structure. An outer branched structure portion is referred to as a set of the outer branched structures.

As described above, the glucan produced by the method of the present invention was found to have an outer branched structure portion and an inner branched cyclic structure portion and to have a degree of polymerization of about 50 or more. The glucan produced by the method of the present invention had an average degree of polymerization of about 900 and the inner branched structure portion thereof had an average degree of polymerization of about 40, so that the degree of polymerization of the outer branched structure portion was predicted to be about 860 in total. This suggests that the glucan produced by using branching enzyme according to the present invention has an inner branched cyclic structure portion and an outer branched structure portion in a ratio of about 1:20 on average.

Example 4: Regulation of Degree of Polymerization of Cyclic Glucan

First, 500 mg of the glucan with an average degree of polymerization of 900 obtained in Example 1 was thoroughly dissolved in 500 μl of DMSO. To this solution, 500 μl of 1M sodium acetate buffer (pH 5.5), 3 ml of distilled water, and 1 ml of 10 units/ml of glucoamylase (Toyobo Co., Ltd.) were added, and the mixture was allowed to react at 40° C. for 3 hours. The reaction solution was heated at 100° C. for 10 minutes, and thereafter, denatured enzyme protein was removed by centrifugation at 10,000 rpm for 15 minutes. The amount of glucose in the supernatant was determined by the Glucostat method. It was found that about 70% glucosyl residue in the glucan obtained in Example 1 was deleted. Ten-fold volume of ethanol was added to the supernatant to precipitate glucan, whereby glucan having a shorter outer branched structure portion was obtained. The glucan thus obtained had an average degree of polymerization of 270.

C. Production method using D-enzyme

Example 5

5-1: Production using D-enzyme

First, 40 mg of commercially available waxy corn starch was suspended in 2 ml of DMSO. Then, 18 ml of 20 mM citrate buffer (pH 7.0) containing 680 units of purified D-enzyme was added to the suspension, and the mixture was allowed to react at 30° C. for 40 hours.

The reaction solution was heated at 100° C. for 10 minutes and centrifuged to remove denatured enzyme protein. Then, 10-fold volume of ethanol was added to the supernatant to precipitate glucan. The precipitate was lyophilized to obtain about 40 mg of glucan powder.

Figure 15:
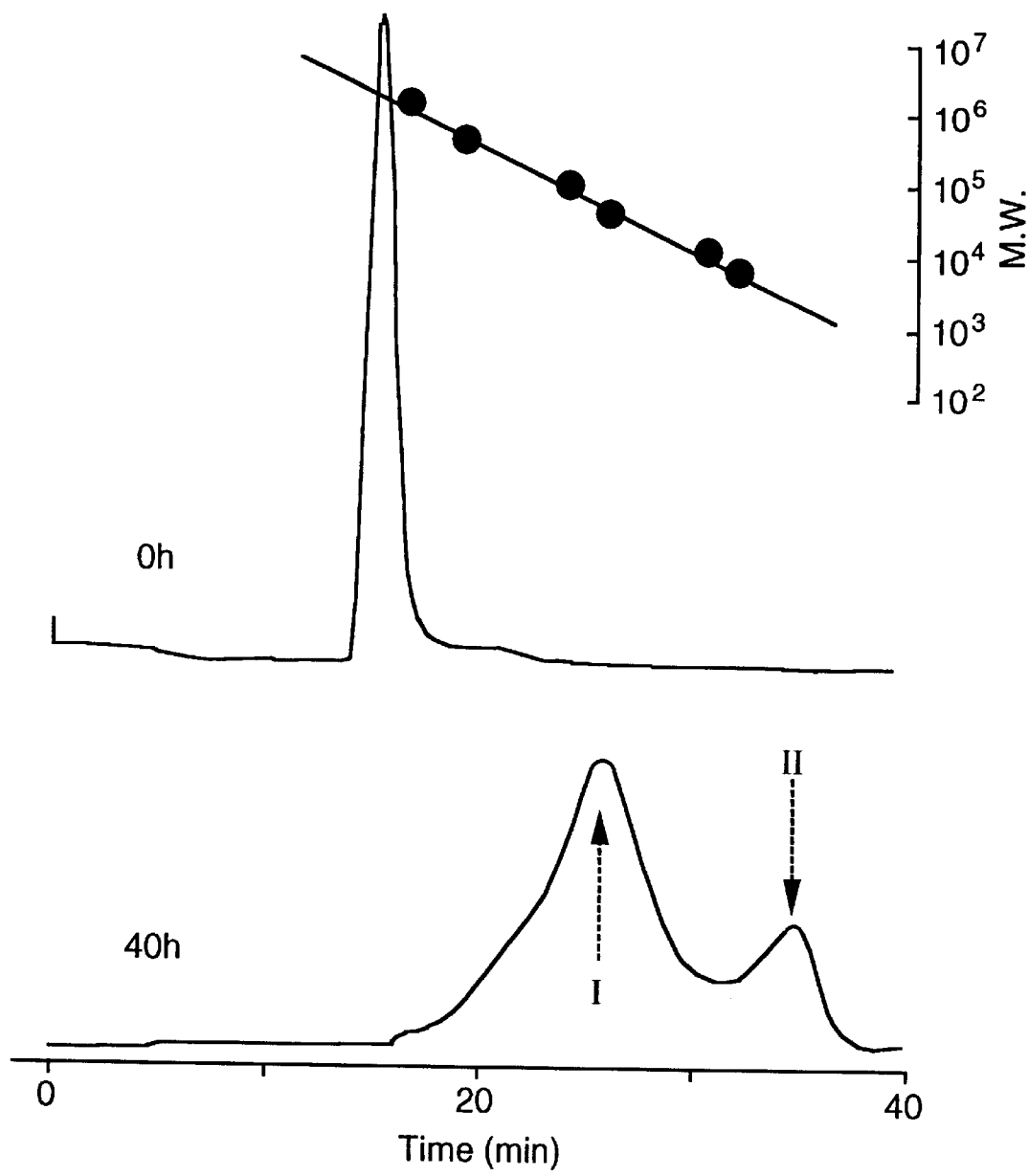
FIG. 15 is a diagram showing gel filtration chromatography of glucan obtained by using D-enzyme.

The precipitate thus obtained was fractionated by gel filtration chromatography. The precipitate was dissolved in 250 μl of distilled water, and a total amount thereof was loaded onto a column obtained by connecting Superose 6 (φ1 cm×30 cm, Pharmacia) to Superdex 30 (φ1 cm×30 cm, Pharmacia). Then, elution was conducted at a flow rate of 1 ml/minute, using 150 mM of sodium acetate aqueous solution. As shown in FIG. 15, amylopectin eluted in a void volume was decomposed into lower molecules by the reaction of D-enzyme, and 2 kinds of components were generated, showing Peak I where an average molecular weight was about 30,000 and Peak II where an average molecular weight was about 3,000. The molecular weight of cyclic glucan is a value calculated using synthetic amylose as standards.

Fractions included in Peaks I and II were respectively collected. Ten-fold volume of ethanol was added to the fractions included in Peak I. Then, the precipitate was collected by centrifugation and lyophilized to obtain 20 mg of glucan. In the similar manner, the precipitate was collected from Peak II and lyophilized to obtain 5 mg of glucan.

Structures of glucans included in Peaks I and II thus separated were analyzed.

5-2: Structural analysis of glucans included in Peak I

The reducing end of the glucans included in Peak I was not detected, and the number of reducing ends did not increase, compared to the raw material, waxy corn starch.

Glucans included in Peak I were treated with glucoamylase under the same condition as that used in 3-2 of Example 3; and as a result, a glucoamylase-resistant component was obtained. The average molecular weight of the glucoamylase-resistant component was about 5,000, which was calculated by using synthetic amylose in the same manner as the above. This value was recognized to be smaller, compared with that before the glucoamylase treatment.

Furthermore, the glucoamylase-resistant component was digested with various kinds of amylases by the same method as that used in 3-4 of Example 3. As a result, the glucoamylase-resistant component was not decomposed by a single use of glucoamylase; however, it was decomposed with α-amylase, i.e., endo-type amylase which hydrolyzes an α-1,4-glucoside bond in a starch molecule, and IMM was detected. The glucoamylase-resistant component was also decomposed by the combined use of isoamylase and glucoamylase. Furthermore, the glucoamylase-resistant component was partially decomposed by a single use of isoamylase to generate oligosaccharide with a degree of polymerization of 3 or more.

From the above, the glucoamylase-resistant component thus obtained was found to have a cyclic structure containing at least one α-1,6-glucoside bond.

Furthermore, glucosyl stubs were confirmed to be present in the glucoamylase-resistant component. Thus, the glucans included in Peak I were concluded to be one having an inner branched cyclic structure portion and an outer branched structure portion.

5-3: Structural analysis of glucans included in Peak II

The reducing end of the glucans included in Peak II was not detected. Most of the glucans included in Peak II did not decrease in molecular weight, even when being treated with glucoamylase. The glucans included in Peak II were completely decomposed with α-amylase which is an endo-type amylase, and IMM was hardly detected. Furthermore, most of the glucans included in Peak II were not decomposed with isoamylase which hydrolyzes a α-1,6-glucoside bond.

From the above, the glucans included in Peak II were concluded to contain cyclic glucan not having a α-1,6-glucoside bond and having only α-1,4-glucoside bonds as its main component.

5-4: Glucan obtained in Example 5

It was concluded that the glucan obtained in Example 5 was a mixture of glucan having only α-1,4-glucoside bonds and glucan having an inner branched cyclic structure portion and an outer branched structure portion.

Example 6: Structure of glucans included in Peak I of Example 5

Glucans included in Peak I were proved to have an inner branched cyclic structure portion and an outer branched structure portion. The outer branched structure portion is completely decomposed into glucose with glucoamylase, and the inner branched cyclic structure portion (glucoamylase-resistant component) remains. Furthermore, the glucoamylase-resistant portion is decomposed with the combined use of debranching enzyme and glucoamylase. By utilizing these characteristics, it is possible to determine a non-cyclic structure portion in glucan, a cyclic structure portion containing an α-1,6-bond, and a cyclic structure portion containing no α-1,6-bond.

First, 10 mg of the glucans included in Peak I obtained in Example 5 and 10 mg of amylopectin were dissolved in 1 ml of DMSO separately, and the mixture was immediately diluted with 8 ml of 100 mM sodium acetate buffer (pH 5.0). Then, 900 μl aliquots of this dilution were dispensed into 4 tubes. Then, 100 μl of (1) distilled water, 100 μl of (2) a glucoamylase solution, 100 μl of (3) a mixed solution of debranching enzyme and glucoamylase, and 100 μl of (4) a mixed solution of endotype α-amylase and glucoamylase were respectively added to the tubes, and the respective mixtures were allowed to react at 40° C. for 4 hours. After the completion of reaction, the amount of glucose generated was measured by using a commercially available glucose measuring kit. The outer branched structure portion in the sample glucan, the inner branched cyclic structure portion, and the cyclic structure portion having only an α-1,4-glucoside bond were respectively calculated in accordance with the following formulae:

$$\text{Outer branched structure portion (\%)} = \frac{x-c}{z-c} \times 100$$

$$\text{Inner branched cyclic structure portion (\%)} = \frac{y-x}{z-c} \times 100$$

$$\text{Cyclic structure portion containing only } \alpha-1,4\text{-glucoside bonds (\%)} = \frac{z-y}{z-c} \times 100$$

where c, x, y, and z represent the amount of glucose generated from the above-mentioned reaction solutions (1), (2), (3), and (4), respectively. Table 1 shows the result.

TABLE 1

|  | Waxy corn starch (%) | Glucans included in Peak I of Example 5 (%) |
|---|---|---|
| Outer branched structure portion | 98.9 | 86.9 |
| Cyclic portion containing no α-1,6-bond | 0.5 | 0.5 |
| Inner branched cyclic structure portion | 0.6 | 12.6 |

This result suggests that the glucans included in Peak I obtained in Example 5 contain at least one α-1,6-glucoside bond, and contain the inner branched cyclic structure portion and the outer branched structure portion in a ratio of about 1:7 on average.

D. Production of glucan using CGTase

Example 7: Method for producing glucan, using CGTase

As a raw material, 40 mg of commercially available waxy corn starch was dissolved with heating in 18 ml of 20 mM sodium acetate buffer (pH 5.5) containing 100 mM NaCl. Separately, purified CGTase was dissolved in 20 mM of sodium acetate buffer (pH 5.5) containing 100 mM of NaCl so as to be 0.2 units/ml. Then, 2 ml of this enzyme solution was added to the raw material solution, and the mixture was allowed to react at 40° C. for 2 hours.

The reaction solution was heated at 100° C. for 10 minutes, and denatured enzyme protein was removed by centrifugation. Ten-fold volume of acetone was added to the supernatant to precipitate glucan.

Example 8: Structural Analysis of Glucan Obtained in Example 7

Figure 16:
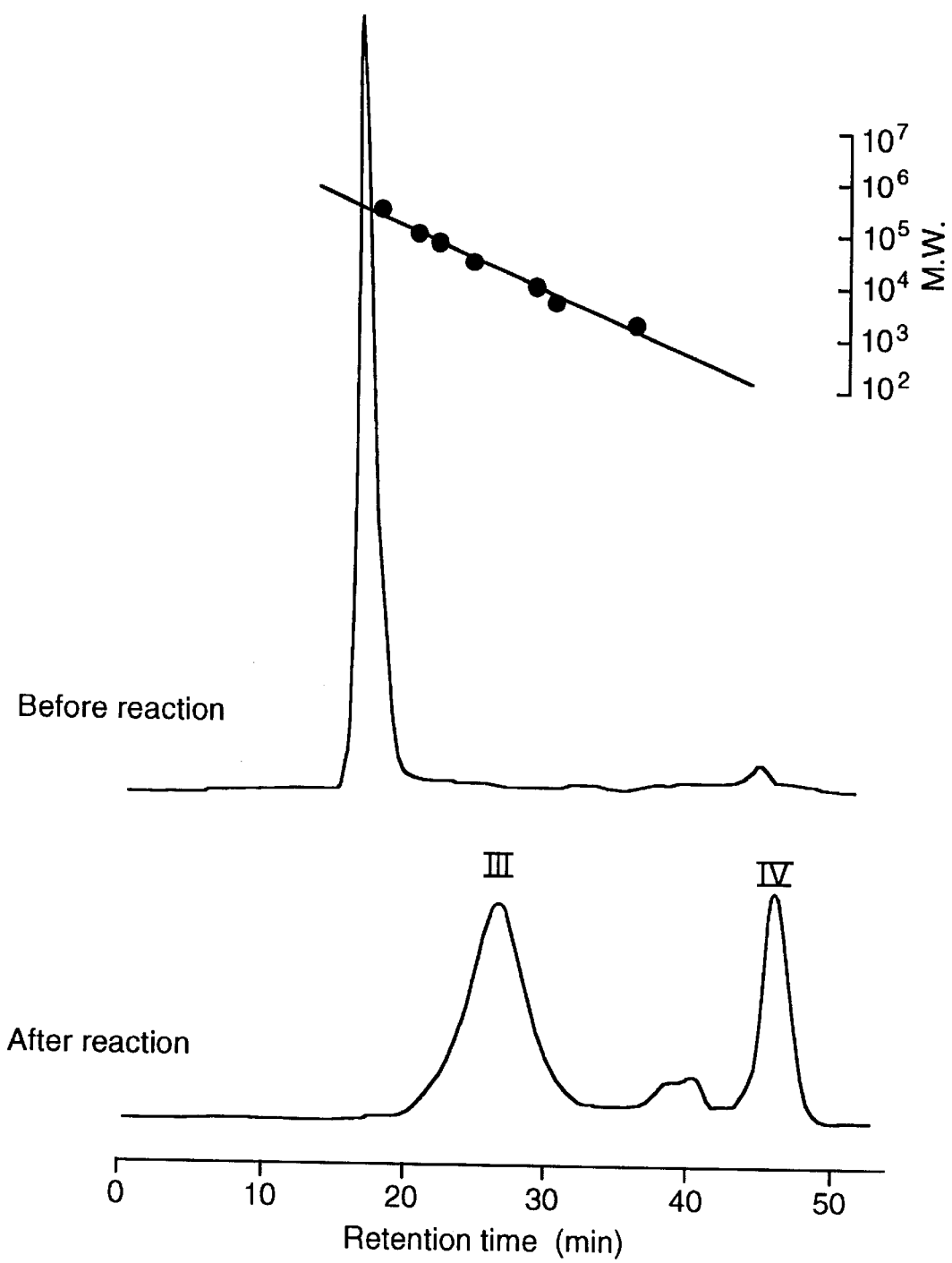
FIG. 16 is a diagram showing gel filtration chromatography of glucan obtained by using CGTage.

The precipitate thus obtained was subjected to gel filtration chromatography. The precipitate was dissolved in 250 μl of distilled water, and the entire amount of the solution was loaded onto connected columns of Superose 6 (φ1 cm×30 cm, Pharmacia) and Superdex 30 (φ1 cm×30 cm, Pharmacia). The elution was conducted with 20 mM of sodium acetate buffer (pH 5.5) containing 100 mM of NaCl at a flow rate of 1 ml/minute. As shown in FIG. 16, amylopectin eluted in a void volume was decomposed into lower molecules by the reaction of CGTase, whereby 2 kinds of components included in Peaks III and IV were generated.

The glucans included in Peaks III and IV were fractionated, precipitated with acetone, collected, and lyophilized, whereby 16 mg and 13 mg of powders were respectively obtained.

The average molecular weight of the glucans included in Peak III was 30,000. The glucans included in Peak IV have a very low molecular weight; thus, they were not be able to be measured according to this method.

8-1 Structural analysis of glucans included in Peak III

Ten-fold volume of ethanol was added to the fractionated glucans included in Peak III to obtain a precipitate. The precipitate was collected by centrifugation and lyophilized, thereby obtaining 16 mg of powdery glucan.

The reducing end of the glucans included in Peak III was not detected, and the number of the reducing end did not increase, compared with the raw material, waxy corn starch.

The glucans included in Peak III were treated with glucoamylase under the same condition as that used in 3-2 of Example 3. As a result, a glucoamylase-resistant component was obtained. The average molecular weight of the glucoamylase-resistant component was about 5,000, which was calculated by using synthetic amylose in the same manner as the above. This value was recognized to be smaller, compared with that before the glucoamylase treatment.

Furthermore, the glucoamylase-resistant component was digested with various kinds of amylases by the same method as that used in 3-4 of Example 3. As a result, the glucoamylase-resistant component was not decomposed with the single use of glucoamylase; however, it was decomposed with α-amylase, i.e., endo-type amylase hydrolyzing an α-1,4-glucoside bond in a starch molecule, and IMM was detected. The glucoamylase-resistant component was also decomposed by the combination of isoamylase and glucoamylase. Furthermore, the glucoamylase-resistant component was partially decomposed with the single use of isoamylase to generate oligosaccharide with a degree of polymerization of 3 or more. Furthermore, glucosyl stubs were confirmed to be present in the glucoamylase-resistant component.

From the above, the glucoamylase-resistant component thus obtained was found to have a cyclic structure containing at least one α-1,6-glucoside bond.

Thus, the glucans included in Peak III were concluded to possess an inner branched cyclic structure portion and an outer branched structure portion.

8-2: Structural analysis of glucans included in Peak IV

The reducing end of the glucans included in Peak IV was not detected. The glucans included in Peak IV did not decrease in molecular weight, even when being treated with glucoamylase. The glucans included in Peak IV were not decomposed with isoamylase cutting an α-1,6-glucoside bond.

From the above, the glucans included in Peak IV were concluded to have a cyclic structure not having a α-1,6-glucoside bond or an outer branched structure, but having only α-1,4-glucoside bonds.

Separately, the glucans included in Peak IV were analyzed with HPLC using a column for sugars; and as a result, 2 peaks were confirmed. Each of the peaks were completely matched with the elution positions of cyclic α-1,4-glucan having a degree of polymerization of 6 and 7, i.e., α-CD and β-CD. Thus, the glucans included in Peak IV were concluded to be a mixture of the conventionally known α-CD and β-CD.

8-3 Structure of the glucan obtained in Example 7

From the above, the glucans obtained in Example 7 were concluded to be a mixture of α-CD and β-CD both having only α-1,4-glucoside bonds and glucan having an inner branched cyclic structure portion and an outer branched structure portion.

Example 9: Structure of Glucans Included in Peak III of Example 7

The inner branched cyclic structure portion and the outer branched structure portion of the glucans included in Peak III obtained in Example 7 were studied in the same way as in Example 6. Table 2 shows the result.

TABLE 2

| | Waxy corn starch (%) | Glucans included in Peak III of Example 7 (%) |
|---|---|---|
| Outer branched structure portion | 98.9 | 87.2 |
| Cyclic portion containing no α-1,6-bond | 0.5 | 0.1 |
| Inner branched cyclic structure portion | 0.6 | 12.7 |

This result shows that the glucans included in Peak III obtained in Example 7 and the glucans included in Peak I obtained in Example 5 are almost the same. That is, the results suggest that the glucans included in Peak III contain at least one α-1,6-glucoside bond and an inner branched cyclic structure portion and an outer branched structure portion in a ratio of about 1:7 on average.

It was proved from the above that glucan having an inner branched cyclic structure portion and an outer branched structure portion can be produced by using branching enzyme, D-enzyme, or CGTase, and almost the same glucan can be produced using different enzymes with similar activity.

Example 10: Solubility of Glucan Obtained by the Method of the Present Invention The glucan of Example 1, the glucan in Peak I of Example 5 and the glucan in Peak III of Example 7 were respectively suspended in distilled water so as to be 10% (w/v). For comparison, waxy corn starch and soluble starch (Wako Pure Chemical Industries, Ltd.) were also respectively suspended in distilled water so as to be 10% (w/v). The respective suspensions were vigorously stirred with a Vortex mixer and centrifuged at 12,000 rpm for 10 minutes to determine sugar concentration dissolved in the supernatant. Table 3 shows the result.

TABLE 3

| | Concentration of sugar dissolved in supernatant (% (w/v)) |
|---|---|
| Glucan of Example 1 | 10 |
| Peak I of Example 5 | 10 |
| Peak III of Example 7 | 10 |
| Soluble starch | 1.2 |
| Waxy corn starch | 0.8 |

Compared with the conventional waxy corn starch and soluble starch, it was found that the solubility of the glucans obtained by the method of the present invention was remarkably high.

Example 11: Retrogradation of the Glucan Obtained in Each Example

The glucan of Example 1, the glucan in Peak I of Example 5, the glucan included in Peak III of Example 7, the conventional waxy corn starch, and the conventional soluble starch (Wako Pure Chemical Industries, Ltd.) were respectively placed in screw vials in 200 mg portions. Then, 10 ml of distilled water was added to each screw vial, and each screw vial was heated in a hot water bath at about 100° C. so as to obtain a solution. Here, since the waxy corn starch had poor solubility, 50 mg thereof was taken and treated in the same way. These solutions were allowed to stand at 4° C., and after a predetermined period of time, 1 ml each of sample was taken and the degree of suspension was measured at 660 nm as an index for retrogradation. Table 4 shows the result.

TABLE 4

|  | Increase in turbidity at 660 nm | |
| --- | --- | --- |
|  | after 1 day | after 2 days |
| Glucan of Example 1 | 0 | 0 |
| Peak I of Example 5 | 0 | 0 |
| Peak III of Example 7 | 0 | 0 |
| Soluble starch | 0.182 | 0.583 |
| Waxy corn starch | 0.012 | 0.023 |

Compared with the conventional waxy corn starch and soluble starch, it was found that the retrogradation of the glucans obtained in the examples was remarkably low.

Example 12: Viscosity of Gelatinized Solution of the Glucans Obtained in the Examples The glucan of Example 1, the glucan in Peak I of Example 5, the glucan included in Peak III of Example 7, the conventional waxy corn starch, the conventional soluble starch (produced by Wako Pure Chemical Industries, Ltd.), and Pinedex #1 (Matsutani Kagaku Kabushikikaisha) were respectively placed in screw vials in 1.6 g portions. Then, 8 ml of distilled water was added to each screw vial to obtain a dispersion, 72 ml of dimethylsulfoxide was added to each dispersion, and each dispersion was thoroughly stirred at room temperature to obtain a solution. The viscosity of each solution was measured by a Digital Viscometer DVL-B (Rotor: No. 1, Rotation number: 60 rpm, measured for 10 seconds, manufactured by Tokyo Keiki). As a control, 8 ml of distilled water with 72 ml of dimethyl sulfoxide (90% DMSO solution) was used. The viscosity of each solution was measured in the same manner. Table 5 shows the result. Pinedex #1 used in the present example is starch more strongly hydrolyzed with α-amylase than the above-mentioned soluble starch.

TABLE 5

|  | Viscosity (mPa · S) |
| --- | --- |
| 90% DMSO solution | 5.3 |
| Glucan of Example 1 | 6.4 |
| Peak I of Example 5 | 6.2 |
| Peak III of Example 7 | 6.1 |
| Pinedex #1 | 5.8 |
| Soluble starch | 5.6 |
| Waxy corn starch | 100.3 |

Compared with the conventional waxy corn starch, it was found that the viscosity of the gelatinized solution of the glucan obtained in each example was remarkably low and showed the similar viscosity to that of Pinedex #1 and the soluble starch.

Example 13: Reactivity of the Glucans Obtained in the Examples

First, 20 mg each of the glucans of Example 1, in Peak I of Example 5 and in Peak III of Example 7, the conventional soluble starch and Pinedex #1 were respectively dissolved in 1 ml of distilled water. The reducing ability of each solution was determined by a dinitrosalicylic acid method (S. Fukui, Biochemical Experiment Method I, Assay of Reducing Sugar, Gakkai Shuppan Center) using glucose as a standard. Table 6 shows the result.

TABLE 6

|  | Amount of reducing sugar (mg/ml) |
| --- | --- |
| Glucan of the present invention | Not detected (<0.01) |
| Peak I of Example 5 | Not detected (<0.01) |
| Peak III of Example 7 | Not detected (<0.01) |
| Pinedex #1 | 5.10 |
| Soluble starch | 2.84 |

Reducing sugar was not detected from the glucan obtained in each example, while reducing sugar was detected from the conventional Pinedex #1 and the soluble starch.

The color causing reaction which occurs between sugar and amino acid (i.e., amino-carbonyl reaction) is a reaction between a reducing group of sugar and an amino acid (O. Igarashi, Food Chemistry, Kogaku Shuppannsha). The glucan obtained in each example had less amount of reducing sugar (reducing sugar was not detected); in other words, the glucan had a lower amount of reducing groups. It was found from this fact that the glucan obtained in each example had low reactivity, compared with the conventional Pinedex #1 and the soluble starch.

Example 14: Preparation of Derivative of Phosphorylated Glucan

First, 8 mg of the glucan obtained in Example 1 was suspended in 1 ml of dimethylformamide and allowed to react with 46 mg of phosphorus hydroxychloride, Then, 9 ml of acetone was added to the reaction solution to obtain 8 mg of derivative of phosphorylated glucan.

Example 15: Effect of Glucan of Example 1 on Suppressing Retrogradation Starch

Figure 17:
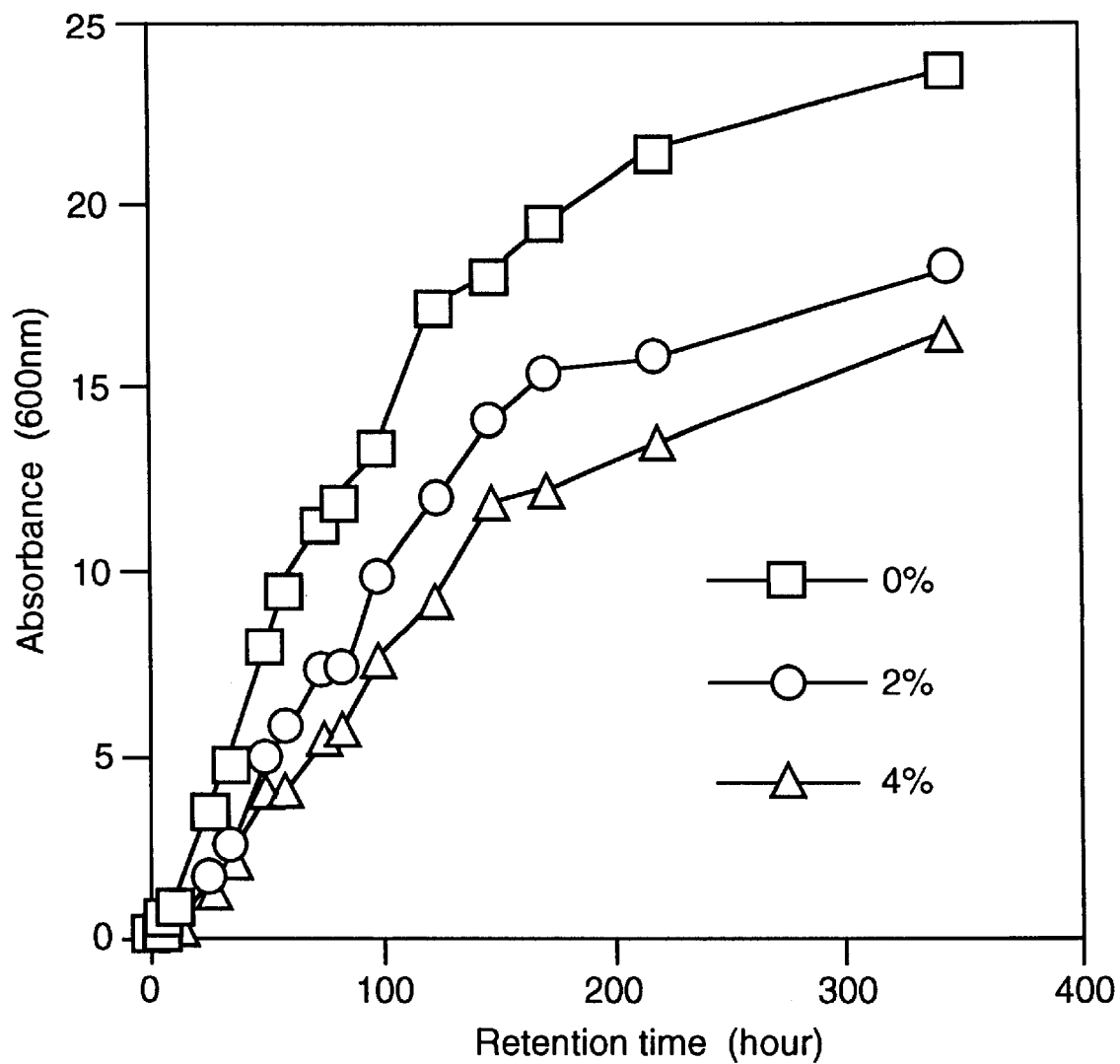
FIG. 17 is a diagram showing that glucan obtained in Example 1 has the effect of suppressing starch retrogradation.

When 4% soluble starch aqueous solution completely gelatinized by heating is kept at 4° C., the soluble starch rapidly retrogrades and the gelatinized solution becomes turbid. Using this system, the effect of suppressing the retrogradation of starch by the glucan obtained in the present invention was studied. The glucan obtained in Example 1 was added to 4% soluble starch aqueous solution so that the final concentration was 0%, 2%, and 4%, respectively, and the solutions were kept at 4° C. Each solution was sampled after a predetermined period of time, and the turbidity of each solution was measured at an absorbance of 660 nm. FIG. 17 shows the result.

It was found that the glucan obtained in Example 1 had an effect of suppressing the retrogradation of starch.

Example 16: Sports Drink Containing the Glucan of the Present Invention

Sports drink containing the following components in the following proportion was prepared, using the glucan obtained in Example 1. It is noted that a unit is a part by weight.

| | |
|---|---|
| Salt | 0.3 |
| Vitamin C | 0.02 |
| Vitamin B1 | 0.02 |
| Magnesium chloride | 0.2 |
| Emulsified calcium | 0.2 |
| Citric acid | 2.0 |
| Sodium citrate | 1.5 |
| Glucose | 50 |
| Water | 1000 |
| Cyclic glucan of Example 1 | 100 |

The sports drink thus obtained had an outstanding digestive property and a high energy conversion efficiency.

Example 17: Adhesive Composition Containing the Glucan of the Present Invention

Sixty parts of water were added to 40 parts of the glucan included in Peak I of Example 5, and the mixture was heated so that the glucan was thoroughly dissolved in water. The solution thus obtained showed satisfactory adhesion.

According to the method of the present invention, the glucan of the present invention can be produced using enzyme whose use has never been considered before. The step of allowing carbohydrate as a raw material having α-1,4-glucoside bonds and at least one α-1,6-glucoside bond to react with enzyme capable of acting on the carbohydrate to form a cyclic structure suffices. Thus, the glucan of the present invention can be very easily produced.

The glucan of the present invention has the following outstanding characteristics: the glucan has remarkably higher solubility in water, compared with the above-mentioned material such as existing starch; a gelatinized solution dissolving the glucan has low viscosity; and the glucan is not likely to retrograde, unlike conventional starch. Furthermore, the glucan of the present invention or derivatives thereof has low reactivity; therefore, when mixed with protein or amino acid and heated, the glucan is not likely to become colored, unlike the existing starch syrups and dextrin.

As described above, because of high solubility in water, the glucan of the present invention can be preferably used for powdered base, coffee, soy sauce, sauce for dipping noodles, Worcestershire sauce, broth stock, stew stock, soup stock, mixed seasonings, curry powder, jelly, caramel, chewing gum, chocolate, cookies, crackers, ice cream, sherbet, juice, powdery juice, a bathing agent, medicine for internal use, powdery medicine, paint, adhesive, thickener, and gelatinized material.

The glucan of the present invention is not likely to retrograde; therefore, it can be preferably used for Japanese confectionery, Western confectionery, frozen foods, cold foods, rice cakes, and rice balls.

Since a gelatinized solution dissolving the glucan of the present invention or derivatives thereof has low viscosity, the glucan or derivatives thereof can be preferably used as a raw material for biodegradable plastic, an intermediate material for producing cyclodextrin from starch, and a material in starch processing industry.

Furthermore, the glucan of the present invention has satisfactory adhesion; thus, it can be effectively used for an adhesive composition.

Still furthermore, the glucan of the present invention has some of the structure as conventional starch, except for a cyclic structure, so that it can be easily decomposed into glucose with enzymes in a living body, that is, the glucan has an outstanding digestive property. Therefore, the glucan of the present invention can be used for sports drinks, sports foods, etc.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing glucan with a degree of polymerization of 50 or more composed of an inner branched cyclic structure portion and an outer branched structure portion, comprising the step of:
    allowing a carbohydrate containing α-1, 4 glucoside bonds and at least one α-1, 6 glucoside bond to react with an enzyme selected from the group consisting of branching enzyme, D-enzyme and cyclodextrin glucanotransferase.

2. The method according to claim 1, wherein the carbohydrate is starch.

3. The method according to claim 1, wherein the carbohydrate is amylopectin.

4. The method according to claim 1, wherein the cyclodextrin glucanotransferase is an enzyme derived from Alkalophilic Bacillus sp. A2-5a.

5. The method according to claim 1, wherein the degree of polymerization of the glucan is in the range of 50 to 5,000.

6. The method according to claim 1, wherein a degree of polymerization of the inner branched cyclic structure portion of the glucan is in the range of 10 to 100.

7. The method according to claim 1, wherein a degree of polymerization of the outer branched structure portion is 40 or more.

8. The method according to claim 7, wherein a degree of polymerization of each unit chain of the outer branched structure portion of the glucan is in the range of 10 to 20 on an average.

9. A method for producing glucan with a degree of polymerization of 50 or more composed of an inner branched cyclic structure portion and an outer branched structure portion, comprising the step of:
    allowing a carbohydrate consisting of α-1, 4 glucoside bonds to react with a branching enzyme.

10. A method for producing a mixture of glucan having a degree of polymerization of 50 or more composed of an inner branched cyclic structure portion and an outer branched structure portion and glucan composed of a cyclic structure containing only α-1, 4 glucoside bonds, the method comprising the step of:
    allowing a carbohydrate containing α-1, 4 glucoside bonds and at least one α-1, 6 glucoside bond to react with an enzyme selected from the group consisting of branching enzyme, D-enzyme and cyclodextrin glucanotransferase.

11. The method according to claim 10, wherein the carbohydrate is starch.

* * * * *

SEQUENCE LISTING

```
<160> NUMBER OF SEQ ID NOS:  4

<210> SEQ ID NO 1
<211> LENGTH: 21
<212> TYPE: DNA
<213> ORGANISM: Unknown (unavailable)
<220> FEATURE:
<221> NAME/KEY: misc_feature
<222> LOCATION: (3)..(3)
<223> OTHER INFORMATION: Y is T or C
<221> NAME/KEY: misc_feature
<222> LOCATION: (18)..(18)
<223> OTHER INFORMATION: Y is T or C
<221> NAME/KEY: misc_feature
<222> LOCATION: (21)..(21)
<223> OTHER INFORMATION: Y is T or C
<221> NAME/KEY: misc_feature
<222> LOCATION: (9)..(9)
<223> OTHER INFORMATION: N is G, A, T or C
<221> NAME/KEY: misc_feature
<222> LOCATION: (12)..(12)
<223> OTHER INFORMATION: N is G, A, T or C
<221> NAME/KEY: misc_feature
<222> LOCATION: (15)..(15)
<223> OTHER INFORMATION: N is G, A, T or C
<221> NAME/KEY: misc_feature
```

```
<222> LOCATION: (14)..(14)
<223> OTHER INFORMATION: S is G or C

<400> SEQUENCE: 1
gaytgggtnc cngsncaytt y                                              21

<210> SEQ ID NO 2
<211> LENGTH: 21
<212> TYPE: DNA
<213> ORGANISM: Unknown (unavailable)
<220> FEATURE:
<221> NAME/KEY: misc_feature
<222> LOCATION: (10)..(10)
<223> OTHER INFORMATION: Y is T or C
<221> NAME/KEY: misc_feature
<222> LOCATION: (4)..(4)
<223> OTHER INFORMATION: N is G, A, T, or C
<221> NAME/KEY: misc_feature
<222> LOCATION: (7)..(7)
<223> OTHER INFORMATION: N is G, A, T, or C
<221> NAME/KEY: misc_feature
<222> LOCATION: (19)..(19)
<223> OTHER INFORMATION: N is G, A, T, or C
<221> NAME/KEY: misc_feature
<222> LOCATION: (20)..(20)
<223> OTHER INFORMATION: S is G or C
<221> NAME/KEY: misc_feature
<222> LOCATION: (21)..(21)
<223> OTHER INFORMATION: W is A or T
<221> NAME/KEY: misc_feature
<222> LOCATION: (1)..(1)
<223> OTHER INFORMATION: R is A or G
<221> NAME/KEY: misc_feature
<222> LOCATION: (13)..(13)
<223> OTHER INFORMATION: R is A or G
<221> NAME/KEY: misc_feature
<222> LOCATION: (16)..(16)
<223> OTHER INFORMATION: R is A or G

<400> SEQUENCE: 2
rtgnacnacy tcrtcrtgns w                                              21

<210> SEQ ID NO 3
<211> LENGTH: 2426
<212> TYPE: DNA
<213> ORGANISM: Bacillus stearothermophilus (Strain TRBE14)
<220> FEATURE:
<221> NAME/KEY: misc_feature
<222> LOCATION: (385)..(392)
<223> OTHER INFORMATION: S SD sequence
<221> NAME/KEY: misc_feature
<222> LOCATION: (402)..(2357)
<223> OTHER INFORMATION: P CDS

<400> SEQUENCE: 3
agcgctaaga catcggaagc catatgggcc gaatcggaca acaaagcgag cgagttcgag      60
agcaccccac cgatgatttc aacaaccgtg aaaaagacgg tgagcacgag tgtaatccaa     120
agcgcctttt tcgactgggt ttgtgttttc acgtgtggaa gatgatgaaa atcgtatgct     180
ccaggagaca taatacacct cttttttata ataattatta atttatatct attaaaatat     240
aaaaagtgct aggtgtgcaa aaaatttatc gacaaatccc acaattttg atggattttg      300 tcaaaaaata tagataattt tttcgaggaa tgcagcggtg aagtggcgaa taaggaataa     360
tgtgtggcca tcatcttgct ttggaaagga tgcgatacgg tttgattgcg gcgaatccga     420
cggatttgga agtgtatttg tttcatgaag gcagcttgta taaagttac gagctgtttg      480 gcgcccatgt gattaatgag ggcgggaagg tcggcacccg ttttgtgtt tgggcgccgc     540 acgcgcgcga ggtgcgtctt gtcggcagtt tcaacgattg ggacgggacg gattttcgcc     600
```

-continued

```
ttgagaaagt gaatgatgaa ggggtatgga cgattgttgt ccccgaaaac ttggaagggc    660
atttatataa gtatgagatt gttacgccgg acggacaggt gctgttcaaa gccgacccgt    720 acgctttta ctccgaattg cgtcctcata ccgcctcgat tgcctacgat ctgaaaggat    780
accagtggaa cgatcaatct tggaagcgga agaagcgacg aaaacggatt tatgatcagc    840
ccatggtgat ttatgaactc catttcggtt cgtggaagaa aaaagatggg cgttttata    900 cgtaccgtga gatggccgat gaactgatct cgtatgtgct cgatcatggg tttacgcaca    960
ttgagttgct tcctctcgtc gagcatccgc tcgaccgctc gtgggctat caaggaacag   1020 ggtattatgc ggtaacgagt cgctatggta cgccacacga cttcatgtac ttcgtcgacc   1080
gttgccatca ggcgggaatc ggggtcatta tggactgggt gccggggcat tttgcaagg   1140 acgcccatgg gttatatatg tttgatggcg ccccgacgta tgaatacgcg aatgaaaaag   1200
accgagaaaa ttacgtttgg gggacggcca attttgattt aggcaagccg gaagtgcgca   1260
gttttctcat ctcgaacgca ttgtttggc tcgagtatta ccatatcgac gggttccggg   1320
tcgatgcggt tgccaatatg ctttattggc cgaacaatga caggctgtac gagaacccgt   1380
atgcggtcga gtttttgcgc aagttaaacg aagcggtgtt tgcctatgat ccgaatgcgc   1440
tgatgattgc ggaagattcg actgactggc cgaaggtgac cgcgccgacg tatgaaggcg   1500
gactcggctt taattataaa tggaacatgg gctggatgaa cgacatgctg aagtacatgg   1560
aaacaccgcc gtatgagcgg aggcatgtgc ataaccaagt aacgttctcc ctcctttatg   1620
cgtattcgga aaattcatt ttgccgtttt cccacgatga agtcgtgcat ggcaaaaaat   1680
cgctgctcaa taaaatgcca gggtcgtatg aagagaagtt cgcccagctg cgcctcttgt   1740
acggctacat gatggctcat ccgggggaaaa agctgttgtt tatgggcaat gaatttgctc   1800
agtttgatga atggaagttt gaggatgaac tcgattgggt gctgtttgat tttgagctgc   1860
accggaagat gaacgattac atgaaagagt taatcgcctg ctataaacgg tataagccgt   1920
tttacgaatt ggatcatgac ccgcaaggat ttgaatggat tgacgttcac aacgctgaac   1980
aaagcatttt ctcattcatc cgccgcggga aaaagaaga tgatgtgctt gttattgttt   2040
gcaatttcac aaatcaggcg tatgacgact acaaagttgg agtgccgttg ctcgtaccgt   2100
atcgggaagt gctgaatagc gatgcggtca cgtttggtgg atcggggcat gtcaatggga   2160
aacggctttc cgccttcaat gagccgtttc atggtaaacc ataccacgtg cgcatgacga   2220
ttccgccatt tggcatttcc atttacggc cagtgcaaaa acgaggggag agaaagcgaa   2280
atgaaaaaga aatgcatcgc catgttattg gccggcgggc aaggaagtcg gcttcgctcg   2340
ctgacgacaa acatcgctaa accggccgtg ccattcggcg ggaagtaccg gatcattgat   2400
tttacattaa gcaattgcac gaattc                                        2426
```

<210> SEQ ID NO 4
<211> LENGTH: 652
<212> TYPE: PRT
<213> ORGANISM: Bacillus stearothermophilus (Strain TRBE14)

<400> SEQUENCE: 4

```
Met Ile Ala Ala Asn Pro Thr Asp Leu Glu Val Tyr Leu Phe His Glu
1               5                   10                  15

Gly Ser Leu Tyr Lys Ser Tyr Glu Leu Phe Gly Ala His Val Ile Asn
                20                  25                  30

Glu Gly Gly Lys Val Gly Thr Arg Phe Cys Val Trp Ala Pro His Ala
            35                  40                  45
```

```
Arg Glu Val Arg Leu Val Gly Ser Phe Asn Asp Trp Asp Gly Thr Asp
    50                  55                  60

Phe Arg Leu Glu Lys Val Asn Asp Gly Val Trp Thr Ile Val Val
65                  70                  75                  80

Pro Glu Asn Leu Glu Gly His Leu Tyr Lys Tyr Glu Ile Val Thr Pro
                85                  90                  95

Asp Gly Gln Val Leu Phe Lys Ala Asp Pro Tyr Ala Phe Tyr Ser Glu
                100                 105                 110

Leu Arg Pro His Thr Ala Ser Ile Ala Tyr Asp Leu Lys Gly Tyr Gln
                115                 120                 125

Trp Asn Asp Gln Ser Trp Lys Arg Lys Arg Lys Arg Ile Tyr
    130                 135                 140

Asp Gln Pro Met Val Ile Tyr Glu Leu His Phe Gly Ser Trp Lys Lys
145                 150                 155                 160

Lys Asp Gly Arg Phe Tyr Thr Tyr Arg Glu Met Ala Asp Glu Leu Ile
                165                 170                 175

Ser Tyr Val Leu Asp His Gly Phe Thr His Ile Glu Leu Leu Pro Leu
                180                 185                 190

Val Glu His Pro Leu Asp Arg Ser Trp Gly Tyr Gln Gly Thr Gly Tyr
            195                 200                 205

Tyr Ala Val Thr Ser Arg Tyr Gly Thr Pro His Asp Phe Met Tyr Phe
        210                 215                 220

Val Asp Arg Cys His Gln Ala Gly Ile Gly Val Ile Met Asp Trp Val
225                 230                 235                 240

Pro Gly His Phe Cys Lys Asp Ala His Gly Leu Tyr Met Phe Asp Gly
                245                 250                 255

Ala Pro Thr Tyr Glu Tyr Ala Asn Glu Lys Asp Arg Glu Asn Tyr Val
                260                 265                 270

Trp Gly Thr Ala Asn Phe Asp Leu Gly Lys Pro Glu Val Arg Ser Phe
            275                 280                 285

Leu Ile Ser Asn Ala Leu Phe Trp Leu Glu Tyr Tyr His Ile Asp Gly
    290                 295                 300

Phe Arg Val Asp Ala Val Ala Asn Met Leu Tyr Trp Pro Asn Asn Asp
305                 310                 315                 320

Arg Leu Tyr Glu Asn Pro Tyr Ala Val Glu Phe Leu Arg Lys Leu Asn
                325                 330                 335

Glu Ala Val Phe Ala Tyr Asp Pro Asn Ala Leu Met Ile Ala Glu Asp
                340                 345                 350

Ser Thr Asp Trp Pro Lys Val Thr Ala Pro Thr Tyr Glu Gly Gly Leu
            355                 360                 365

Gly Phe Asn Tyr Lys Trp Asn Met Gly Trp Met Asn Asp Met Leu Lys
    370                 375                 380

Tyr Met Glu Thr Pro Pro Tyr Glu Arg Arg His Val His Asn Gln Val
385                 390                 395                 400

Thr Phe Ser Leu Leu Tyr Ala Tyr Ser Glu Asn Phe Ile Leu Pro Phe
                405                 410                 415

Ser His Asp Glu Val Val His Gly Lys Lys Ser Leu Leu Asn Lys Met
                420                 425                 430

Pro Gly Ser Tyr Glu Glu Lys Phe Ala Gln Leu Arg Leu Leu Tyr Gly
            435                 440                 445

Tyr Met Met Ala His Pro Gly Lys Lys Leu Leu Phe Met Gly Asn Glu
        450                 455                 460
```

```
                              -continued

Phe Ala Gln Phe Asp Glu Trp Lys Phe Glu Asp Glu Leu Asp Trp Val
465             470             475             480

Leu Phe Asp Phe Glu Leu His Arg Lys Met Asn Asp Tyr Met Lys Glu
            485             490             495

Leu Ile Ala Cys Tyr Lys Arg Tyr Lys Pro Phe Tyr Glu Leu Asp His
            500             505             510

Asp Pro Gln Gly Phe Glu Trp Ile Asp Val His Asn Ala Glu Gln Ser
            515             520             525

Ile Phe Ser Phe Ile Arg Arg Gly Lys Lys Glu Asp Asp Val Leu Val
            530             535             540

Ile Val Cys Asn Phe Thr Asn Gln Ala Tyr Asp Asp Tyr Lys Val Gly
545             550             555             560

Val Pro Leu Leu Val Pro Tyr Arg Glu Val Leu Asn Ser Asp Ala Val
            565             570             575

Thr Phe Gly Gly Ser Gly His Val Asn Gly Lys Arg Leu Ser Ala Phe
            580             585             590

Asn Glu Pro Phe His Gly Lys Pro Tyr His Val Arg Met Thr Ile Pro
            595             600             605

Pro Phe Gly Ile Ser Ile Leu Arg Pro Val Gln Lys Arg Gly Glu Arg
            610             615             620

Lys Arg Asn Glu Lys Glu Met His Arg His Val Ile Gly Arg Arg Ala
625             630             635             640

Arg Lys Ser Ala Ser Leu Ala Asp Asp Lys His Arg
            645             650
```